(12) United States Patent
Kumar et al.

(10) Patent No.: US 9,988,638 B2
(45) Date of Patent: Jun. 5, 2018

(54) SYNTHETIC BI-DIRECTIONAL PLANT PROMOTER

(71) Applicant: Dow AgroSciences LLC, Indianapolis, IN (US)

(72) Inventors: Sandeep Kumar, Carmel, IN (US); Toby Cicak, Whitestown, IN (US); Heather Leigh Robinson, Indianapolis, IN (US); Dayakar Reddy Pareddy, Carmel, IN (US); Wei Chen, Carmel, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 183 days.

(21) Appl. No.: 14/938,643

(22) Filed: Nov. 11, 2015

(65) Prior Publication Data

US 2016/0130595 A1    May 12, 2016

Related U.S. Application Data

(60) Provisional application No. 62/078,205, filed on Nov. 11, 2014.

(51) Int. Cl.
  *C12N 15/82* (2006.01)
(52) U.S. Cl.
  CPC ................. *C12N 15/8216* (2013.01)
(58) Field of Classification Search
  None
  See application file for complete search history.

(56) References Cited

U.S. PATENT DOCUMENTS

| | | | |
|---|---|---|---|
| 6,388,170 B1* | 5/2002 | Gan | C12N 15/8216 435/468 |
| 7,838,733 B2 | 11/2010 | Wright | |
| 8,686,222 B2 | 4/2014 | Jayakumar et al. | |
| 2003/0199681 A1* | 10/2003 | Fincher | C12N 9/1092 536/23.2 |
| 2005/0118432 A1* | 6/2005 | Bisazza | B44C 1/14 428/432 |
| 2005/0188432 A1 | 8/2005 | Zhijian et al. | |
| 2013/0254943 A1 | 9/2013 | Kumar et al. | |

FOREIGN PATENT DOCUMENTS

WO    2014039872    3/2014

OTHER PUBLICATIONS

Civan & Svec, Genomics 52:294-97 (2009).*
Dhadi et al., Gene 429:65-73 (2009).*
Das et al., Nucl Acids Res 14(3):1355-64 (1986).*
Potenza et al., In Vitro Cell Dev Biol Plant 40:1-22 (2004).*
Maiti et al., Transgen Res 6:143-156 (1997).*
Donald & Cashmore, EMBO J 9:1717-26 (1990).*
Parra et al., Nucl Acids Res 39(13):5328-37 (2011).*
Binns, Trends Plant Sci 7(5):231-33 (2002).*
Norris et al., Plant Mol Biol 21:895-06 (1993).*
Herman et al., GM Crops 1(5):294-311 (2010).*
International Search Report and Written Opinion for International Application No. PCT/US2015/060134, dated Feb. 24, 2016.
Li, Zhijian T. et al., 'Bi-directional duplex promoters with duplicated enhancers significantly increase transgene expression in grape and tobacco', Transgenic Research, Apr. 2004, vol. 13, No. 2, pp. 143-154.

* cited by examiner

*Primary Examiner* — Cathy Kingdon Worley
*Assistant Examiner* — Russell T Boggs
(74) *Attorney, Agent, or Firm* — Marcos P. Rivas; Magleby Cataxinos & Greenwood

(57) ABSTRACT

This disclosure concerns compositions and methods for promoting transcription of a nucleotide sequence in a plant or plant cell, employing a minimal core promoter element from a *Arabidopsis thaliana* Ubiquitin-10 gene promoter or Cassava Vein Mosaic Virus promoter, and the full-length nucleotide sequence elements from a Cassava Vein Mosaic Virus promoter. Some embodiments relate to a synthetic CsVMV bi-directional promoter that functions in plants to promote transcription of two operably linked nucleotide sequences.

37 Claims, 3 Drawing Sheets

```
                       SEQUENCE LISTING

<160> NUMBER OF SEQ ID NOS: 23

<210> SEQ ID NO 1
<211> LENGTH: 140
<212> TYPE: DNA
<213> ORGANISM: Arabidopsis thaliana

<400> SEQUENCE: 1
actttgcgtg taaacaacgc tcaatacacg tgtcatttta ttattagcta ttgcttcacc    60
gccttagctt tctcgtgacc tagtcgtcct cgtcttttct tcttcttctt ctataaaaca   120
atacccaaag cttcttcttc                                                140

<210> SEQ ID NO 2
<211> LENGTH: 304
<212> TYPE: DNA
<213> ORGANISM: Arabidopsis thaliana

<400> SEQUENCE: 2
gtaaatttct gtgttcctta ttctctcaaa atcttcgatt ttgttttcgt tcgatcccaa    60
tttcgtatat gttctttggt ttagattctg ttaatcttag atcgaagacg attttctggg   120
tttgatcgtt agatatcatc ttaattctcg attagggttt cataaatatc atccgatttg   180
ttcaaataat ttgagttttg tcgaataatt actcttcgat ttgtgatttc tatctagatc   240
tggtgttagt ttcagtttg tgcgatcgaa tttgtcgatt aatctgagtt tttctgatta   300
acag                                                                304

<210> SEQ ID NO 3
<211> LENGTH: 66
<212> TYPE: DNA
<213> ORGANISM: Arabidopsis thaliana

<400> SEQUENCE: 3
acaattcaga tttcaatttc tcaaaatctt aaaaactttc tctcaattct ctctaccgtg    60
atcaag                                                               66

<210> SEQ ID NO 4
<211> LENGTH: 812
<212> TYPE: DNA
<213> ORGANISM: Arabidopsis thaliana

<400> SEQUENCE: 4
gtcgacctgc aggtcaacgg atcaggatat tcttgtttaa gatgttgaac tctatggagg    60
```

```
tttgtatgaa ctgatgatct aggaccggat aagttccctt cttcatagcg aacttattca    120
aagaatgttt tgtgtatcat tcttgttaca ttgttattaa tgaaaaaata ttattggtca    180
ttggactgaa cacgagtgtt aaatatggac caggccccaa ataagatcca ttgatatatg    240
aattaaataa caagaataaa tcgagtcacc aaaccacttg cctttttttaa cgagacttgt   300 tcaccaactt gatacaaaag tcattatcct atgcaaatca ataatcatac aaaaatatcc    360
aataacacta aaaattaaa agaaatggat aatttcacaa tatgttatac gataaagaag     420
ttacttttcc aagaaattca ctgattttat aagcccactt gcattagata aatggcaaaa    480
aaaaacaaaa aggaaaagaa ataaagcacg aagaattcta gaaaatacga aatacgcttc    540
aatgcagtgg gacccacggt tcaattattg ccaattttca gctccaccgt atatttaaaa    600
aataaaacga taatgctaaa aaaatataaa tcgtaacgat cgttaaatct caacggctgg    660
atcttatgac gaccgttaga aattgtggtt gtcgacgagt cagtaataaa cggcgtcaaa    720
gtggttgcag ccggcacaca cgagtcgtgt ttatcaactc aaagcacaaa tacttttcct    780
caacctaaaa ataaggcaat tagccaaaaa ca                                  812

<210> SEQ ID NO 5
<211> LENGTH: 123
<212> TYPE: DNA
<213> ORGANISM: Cassava vein mosaic virus

<400> SEQUENCE: 5
gcggaaagta accttatcac aaaggaatct tatcccccac tacttatcct tttatatttt    60
tccgtgtcat ttttgcccctt gagttttcct atataaggaa ccaagttcgg catttgtgaa   120
aac                                                                 123

<210> SEQ ID NO 6
<211> LENGTH: 74
<212> TYPE: DNA
<213> ORGANISM: Cassava vein mosaic virus

<400> SEQUENCE: 6
aagaaaaaat ttggtgtaag ctattttctt tgaagtactg aggatacaac ttcagagaaa    60
tttgtaagtt tgta                                                     74

<210> SEQ ID NO 7
<211> LENGTH: 320
<212> TYPE: DNA
<213> ORGANISM: Cassava vein mosaic virus

<400> SEQUENCE: 7
ccagaaggta attatccaag atgtagcatc aagaatccaa tgtttacggg aaaaactatg    60
gaagtattat gtgagctcag caagaagcag atcaatatgc ggcacatatg caacctatgt    120
tcaaaaatga agaatgtaca gatacaagat cctatactgc cagatacga agaagaatac    180 gtagaaattg aaaagaaga accaggcgaa gaaaagaatc ttgaagacgt aagcactgac    240
gacaacaatg aaaagaagaa gataaggtcg gtgattgtga agagacata gaggacacat    300 gtaaggtgga aaatgtaagg                                               320

<210> SEQ ID NO 8
<211> LENGTH: 1322
<212> TYPE: DNA
<213> ORGANISM: Arabidopsis thaliana

<400> SEQUENCE: 8
```

```
gtcgacctgc aggtcaacgg atcaggatat tcttgtttaa gatgttgaac tctatggagg      60
tttgtatgaa ctgatgatct aggaccggat aagttccctt cttcatagcg aacttattca     120
aagaatgttt tgtgtatcat tcttgttaca ttgttattaa tgaaaaaata ttattggtca     180
ttggactgaa cacgagtgtt aaatatggac caggccccaa ataagatcca ttgatatatg     240
aattaaataa caagaataaa tcgagtcacc aaaccacttg cctttttaa cgagacttgt      300 tcaccaactt gatacaaaag tcattatcct atgcaaatca ataatcatac aaaaatatcc     360
aataacacta aaaattaaa agaaatggat aatttcacaa tatgttatac gataaagaag      420 ttactttcc aagaaattca ctgattttat agcccactt gcattagata aatggcaaaa       480 aaaacaaaa aggaaaagaa ataaagcacg aagaattcta gaaaatacga aatacgcttc      540
aatgcagtgg gacccacggt tcaattattg ccaattttca gctccaccgt atatttaaaa    600
aataaaacga taatgctaaa aaaatataaa tcgtaacgat cgttaaatct caacggctgg    660
atcttatgac gaccgttaga aattgtggtt gtcgacgagt cagtaataaa cggcgtcaaa    720
gtggttgcag ccggcacaca cgagtcgtgt ttatcaactc aaagcacaaa tacttttcct    780
caacctaaaa ataaggcaat tagccaaaaa caactttgcg tgtaaacaac gctcaataca    840
cgtgtcattt tattattagc tattgcttca ccgccttagc tttctcgtga cctagtcgtc    900
ctcgtctttt cttcttcttc ttctataaaa caatacccaa agcttcttct tcacaattca    960
gatttcaatt tctcaaaatc ttaaaaactt tctctcaatt ctctctaccg tgatcaaggt   1020
aaatttctgt gttccttatt ctctcaaaat cttcgatttt gttttcgttc gatcccaatt   1080
tcgtatatgt tctttggttt agattctgtt aatcttagat cgaagacgat tttctgggtt   1140
tgatcgttag atatcatctt aattctcgat tagggtttca taaatatcat ccgatttgtt   1200
caaataattt gagttttgtc gaataattac tcttcgattt gtgatttcta tctagatctg   1260
gtgttagttt ctagtttgtg cgatcgaatt tgtcgattaa tctgagtttt tctgattaac   1320
ag                                                                   1322

<210> SEQ ID NO 9
<211> LENGTH: 517
<212> TYPE: DNA
<213> ORGANISM: Cassava vein mosaic virus

<400> SEQUENCE: 9
ccagaaggta attatccaag atgtagcatc aagaatccaa tgtttacggg aaaaactatg      60
gaagtattat gtgagctcag caagaagcag atcaatatgc ggcacatatg caacctatgt     120
tcaaaaatga agaatgtaca gatacaagat cctatactgc cagaatacga agaagaatac     180
gtagaaattg aaaagaaga accaggcgaa gaaaagaatc ttgaagacgt aagcactgac     240
gacaacaatg aaaagaagaa gataaggtcg gtgattgtga agagacata gaggacacat     300 gtaaggtgga aatgtaagg gcggaaagta accttatcac aaaggaatct tatccccac      360 tacttatcct tttatatttt tccgtgtcat ttttgcccctt gagttttcct atataaggaa    420
ccaagttcgg catttgtgaa aacaagaaaa aatttggtgt aagctatttt ctttgaagta    480
ctgaggatac aacttcagag aaatttgtaa gtttgta                             517

<210> SEQ ID NO 10
<211> LENGTH: 1519
<212> TYPE: DNA
<213> ORGANISM: Artificial Sequence
<220> FEATURE:
```

-continued

<223> OTHER INFORMATION: synthetic CsVMV bi-directional polynucleotide promoter

<400> SEQUENCE: 10

```
tacaaactta caaatttctc tgaagttgta tcctcagtac ttcaaagaaa atagcttaca     60
ccaaattttt tcttgttttc acaaatgccg aacttggttc cttatatagg aaaactcaag    120
ggcaaaaatg acacggaaaa atataaaagg ataagtagtg ggggataaga ttcctttgtg    180
ataaggttac tttccgcgtc gacctgcagg tcaacggatc aggatattct tgtttaagat    240
gttgaactct atggaggttt gtatgaactg atgatctagg accggataag ttcccttctt    300
catagcgaac ttattcaaag aatgttttgt gtatcattct tgttacattg ttattaatga    360
aaaaatatta ttggtcattg gactgaacac gagtgttaaa tatggaccag gccccaaata    420
agatccattg atatatgaat taaataacaa gaataaatcg agtcaccaaa ccacttgcct    480
tttttaacga gacttgttca ccaacttgat acaaaagtca ttatcctatg caaatcaata    540
atcatacaaa aatatccaat aacactaaaa aattaaaaga aatggataat ttcacaatat    600
gttatacgat aaagaagtta cttttccaag aaattcactg attttataag cccacttgca    660
ttagataaat ggcaaaaaaa aacaaaaagg aaaagaaata aagcacgaag aattctagaa    720
aatacgaaat acgcttcaat gcagtgggac ccacggttca attattgcca attttcagct    780
ccaccgtata tttaaaaaat aaaacgataa tgctaaaaaa atataaatcg taacgatcgt    840
taaatctcaa cggctggatc ttatgacgac cgttagaaat tgtggttgtc gacgagtcag    900
taataaacgg cgtcaaagtg gttgcagccg gcacacacga gtcgtgttta tcaactcaaa    960
gcacaaatac ttttcctcaa cctaaaaata aggcaattag ccaaaaacaa ctttgcgtgt   1020
aaacaacgct caatacacgt gtcattttat tattagctat tgcttcaccg ccttagcttt   1080
ctcgtgacct agtcgtcctc gtcttttctt cttcttcttc tataaaacaa tacccaaagc   1140
ttcttcttca caattcagat ttcaatttct caaaatctta aaaactttct ctcaattctc   1200
tctaccgtga tcaaggtaaa tttctgtgtt ccttattctc tcaaaatctt cgattttgtt   1260
ttcgttcgat cccaatttcg tatatgttct ttggtttaga ttctgttaat cttagatcga   1320
agacgatttt ctgggtttga tcgttagata tcatcttaat tctcgattag ggtttcataa   1380
atatcatccg atttgttcaa ataatttgag ttttgtcgaa taattactct tcgatttgtg   1440
atttctatct agatctggtg ttagtttcta gtttgtgcga tcgaatttgt cgattaatct   1500
gagtttttct gattaacag                                                1519
```

<210> SEQ ID NO 11
<211> LENGTH: 1832
<212> TYPE: DNA
<213> ORGANISM: Artificial Sequence
<220> FEATURE:
<223> OTHER INFORMATION: synthetic CsVMV bi-directional polynucleotide promoter

<400> SEQUENCE: 11

```
ctgttaatca gaaaaactca gattaatcga caaattcgat cgcacaaact agaaactaac     60
accagatcta gatagaaatc acaaatcgaa gagtaattat tcgacaaaac tcaaattatt    120
tgaacaaatc ggatgatatt tatgaaaccc taatcgagaa ttaagatgat atctaacgat    180
caaacccaga aaatcgtctt cgatctaaga ttaacagaat ctaaaccaaa gaacatatac    240
gaaattggga tcgaacgaaa acaaaatcga agattttgag agaataagga acacagaaat    300
ttaccttgat cacggtagag agaattgaga gaaagttttt aagattttga gaaattgaaa    360
```

```
tctgaattgt gaagaagaag ctttgggtat tgttttatag aagaagaaga agaaaagacg      420
aggacgacta ggtcacgaga aagctaaggc ggtgaagcaa tagctaataa taaaatgaca      480
cgtgtattga gcgttgttta cacgcaaagt gtcgacctgc aggtcaacgg atcaggatat      540
tcttgtttaa gatgttgaac tctatggagg tttgtatgaa ctgatgatct aggaccggat      600
aagttccctt cttcatagcg aacttattca agaatgtttt tgtgtatcat tcttgttaca      660
ttgttattaa tgaaaaaata ttattggtca ttggactgaa cacgagtgtt aaatatggac      720
caggccccaa ataagatcca ttgatatatg aattaaataa caagaataaa tcgagtcacc      780
aaaccacttg ccttttttaa cgagacttgt tcaccaactt gatacaaaag tcattatcct      840
atgcaaatca ataatcatac aaaaatatcc aataacacta aaaattaaa agaaatggat       900 aatttcacaa tatgttatac gataaagaag ttacttttcc aagaaattca ctgattttat      960
aagcccactt gcattagata aatggcaaaa aaaacaaaa aggaaaagaa ataaagcacg      1020
aagaattcta gaaatacga aatacgcttc aatgcagtgg gacccacggt tcaattattg      1080
ccaattttca gctccaccgt atatttaaaa ataaaacga taatgctaaa aaaatataaa       1140
tcgtaacgat cgttaaatct caacggctgg atcttatgac gaccgttaga aattgtggtt      1200
gtcgacgagt cagtaataaa cggcgtcaaa gtggttgcag ccggcacaca cgagtcgtgt      1260
ttatcaactc aaagcacaaa tactttttcct caacctaaaa ataaggcaat tagccaaaaa     1320
caactttgcg tgtaaacaac gctcaataca cgtgtcattt tattattagc tattgcttca     1380
ccgccttagc tttctcgtga cctagtcgtc ctcgtctttt cttcttcttc ttctataaaa     1440
caatacccaa agcttcttct tcacaattca gatttcaatt tctcaaaatc ttaaaaactt     1500
tctctcaatt ctctctaccg tgatcaaggt aaatttctgt gttccttatt ctctcaaaat     1560 cttcgattt gttttcgttc gatcccaatt tcgtatatgt tctttggttt agattctgtt      1620
aatcttagat cgaagacgat tttctgggtt tgatcgttag atatcatctt aattctcgat     1680
tagggtttca taaatatcat ccgatttgtt caaataattt gagttttgtc gaataattac     1740
tcttcgattt gtgatttcta tctagatctg gtgttagttt ctagtttgtg cgatcgaatt     1800
tgtcgattaa tctgagtttt tctgattaac ag                                    1832

<210> SEQ ID NO 12
<211> LENGTH: 1027
<212> TYPE: DNA
<213> ORGANISM: Artificial Sequence
<220> FEATURE:
<223> OTHER INFORMATION: synthetic CsVMV bi-directional polynucleotide
      promoter

<400> SEQUENCE: 12
ctgttaatca gaaaactca gattaatcga caaattcgat cgcacaaact agaaactaac        60
accagatcta gatagaaatc acaaatcgaa gagtaattat tcgacaaaac tcaaattatt      120
tgaacaaatc ggatgatatt tatgaaaccc taatcgagaa ttaagatgat atctaacgat     180
caaacccaga aaatcgtctt cgatctaaga ttaacagaat ctaaaccaaa gaacatatac     240
gaaattggga tcgaacgaaa acaaaatcga agatttgag agaataagga acacagaaat      300
ttaccttgat cacggtagag agaattgaga gaagttttt aagatttga gaaattgaaa       360 tctgaattgt gaagaagaag ctttgggtat tgttttatag aagaagaaga agaaaagacg     420
aggacgacta ggtcacgaga aagctaaggc ggtgaagcaa tagctaataa taaaatgaca     480
cgtgtattga gcgttgttta cacgcaaagt ccagaaggta attatccaag atgtagcatc     540
```

```
aagaatccaa tgtttacggg aaaaactatg gaagtattat gtgagctcag caagaagcag        600
atcaatatgc ggcacatatg caacctatgt tcaaaaatga agaatgtaca gatacaagat        660
cctatactgc cagaatacga agaagaatac gtagaaattg aaaagaaga accaggcgaa         720 gaaaagaatc ttgaagacgt aagcactgac gacaacaatg aaaagaagaa gataaggtcg        780
gtgattgtga agagacata gaggacacat gtaaggtgga aaatgtaagg gcggaaagta         840
accttatcac aaaggaatct tatcccccac tacttatcct tttatatttt tccgtgtcat        900 ttttgcccctt gagttttcct ataaaggaa ccaagttcgg catttgtgaa aacaagaaaa        960
aatttggtgt aagctatttt ctttgaagta ctgaggatac aacttcagag aaatttgtaa       1020
gtttgta                                                                 1027

<210> SEQ ID NO 13
<211> LENGTH: 714
<212> TYPE: DNA
<213> ORGANISM: Artificial Sequence
<220> FEATURE:
<223> OTHER INFORMATION: synthetic CsVMV bi-directional polynucleotide
      promoter

<400> SEQUENCE: 13
tacaaactta caaatttctc tgaagttgta tcctcagtac ttcaaagaaa atagcttaca         60
ccaaattttt tcttgttttc acaaatgccg aacttggttc cttatatagg aaaactcaag        120
ggcaaaaatg acacggaaaa atataaaagg ataagtagtg ggggataaga ttcctttgtg        180
ataaggttac tttccgccca gaaggtaatt atccaagatg tagcatcaag aatccaatgt        240
ttacgggaaa aactatggaa gtattatgtg agctcagcaa gaagcagatc aatatgcggc        300
acatatgcaa cctatgttca aaaatgaaga atgtacagat acaagatcct atactgccag        360
aatacgaaga gaatacgta gaaattgaaa agaagaacc aggcgaagaa aagaatcttg         420
aagacgtaag cactgacgac aacaatgaaa agaagaagat aaggtcggtg attgtgaaag        480
agacatagag gacacatgta aggtggaaaa tgtaagggcg gaaagtaacc ttatcacaaa        540
ggaatcttat cccccactac ttatcctttt atattttttcc gtgtcatttt tgcccttgag       600
ttttcctata aaggaacca gttcggcat tgtgaaaac aagaaaaaat tggtgtaag           660 ctattttctt tgaagtactg aggatacaac ttcagagaaa tttgtaagtt tgta              714

<210> SEQ ID NO 14
<211> LENGTH: 1789
<212> TYPE: DNA
<213> ORGANISM: Artificial Sequence
<220> FEATURE:
<223> OTHER INFORMATION: Gene expression cassette of pDAB113190

<400> SEQUENCE: 14
ccagaaggta attatccaag atgtagcatc aagaatccaa tgtttacggg aaaaactatg         60
gaagtattat gtgagctcag caagaagcag atcaatatgc ggcacatatg caacctatgt        120
tcaaaaatga agaatgtaca gatacaagat cctatactgc cagaatacga agaagaatac        180
gtagaaattg aaaagaaga accaggcgaa gaaaagaatc ttgaagacgt aagcactgac         240
gacaacaatg aaaagaagaa gataaggtcg gtgattgtga agagacata gaggacacat        300 gtaaggtgga aaatgtaagg gcggaaagta accttatcac aaaggaatct tatcccccac        360
tacttatcct tttatatttt tccgtgtcat ttttgcccctt gagttttcct ataaaggaa       420 ccaagttcgg catttgtgaa aacaagaaaa aatttggtgt aagctatttt ctttgaagta        480
```

```
ctgaggatac aacttcagag aaatttgtaa gtttgtataa ttagttagat ctccatgtct    540
gaactcatca aagagaacat gcacatgaag ttgtacatgg aaggcacagt caacaatcat    600
cacttcaagt gcacatctga gggagaaggc aaaccctatg aaggcactca gaccatgaag    660
atcaaagttg tggaaggtgg accacttccc tttgcattcg acattcttgc cacaagtttc    720
atgtatgggt caaaggcatt catcaaccac acccaaggga taccagactt tttcaaacaa    780
agctttcctg aaggcttcac atgggagagg ataacaacct atgaggatgg tggagttctg    840
actgccactc aagatacctc tttccagaat ggctgcatta tctacaatgt caagatcaat    900
ggtgtgaact ttccgtccaa tggtcctgtc atgcaaaaga aaacaagagg gtgggaagcc    960
aacactgaga tgttgtaccc agctgatggt ggactgagag acattcaca aatggctctg    1020 aaactcgttg gtggaggcta cttgcattgt agtttcaaga ctacctatcg atccaagaaa    1080
ccagccaaga atctcaagat gcctgggttt cactttgtgg atcatcgttt ggagaggatt    1140
aaggaggctg acaaagaaac ctatgtggag cagcatgaga tggcagttgc taagtactgt    1200
gatcttccga gcaaacttgg acaccgatga gtagttagct aatcaccta gagctcggtc    1260 accagcataa tttttattaa tgtactaaat tactgttttg ttaaatgcaa ttttgctttc    1320
tcgggatttt aatatcaaaa tctatttaga aatacacaat attttgttgc aggcttgctg    1380
gagaatcgat ctgctatcat aaaaattaca aaaaatttt atttgcctca attattttag    1440
gattggtatt aaggacgctt aaattatttg tcgggtcact acgcatcatt gtgattgaga    1500
agatcagcga tacgaaatat tcgtagtact atcgataatt tatttgaaaa ttcataagaa    1560
aagcaaacgt tacatgaatt gatgaaacaa tacaaagaca gataaagcca cgcacattta    1620
ggatattggc cgagattact gaatattgag taagatcacg gaatttctga caggagcatg    1680
tcttcaattc agcccaaatg gcagttgaaa tactcaaacc gccccatatg caggagcgga    1740
tcattcattg tttgtttggt tgcctttgcc aacatgggag tccaaggtt               1789
```

<210> SEQ ID NO 15
<211> LENGTH: 1523
<212> TYPE: DNA
<213> ORGANISM: Artificial Sequence
<220> FEATURE:
<223> OTHER INFORMATION: Gene expression cassette of pDAB113188

<400> SEQUENCE: 15

```
ccagaaggta attatccaag atgtagcatc aagaatccaa tgtttacggg aaaaactatg     60
gaagtattat gtgagctcag caagaagcag atcaatatgc ggcacatatg caacctatgt    120
tcaaaaatga agaatgtaca gatacaagat cctatactgc cagaatacga agaagaatac    180
gtagaaattg aaaagaagaa accaggcgaa gaaaagaatc ttgaagacgt aagcactgac    240
gacaacaatg aaaagaagaa gataaggtcg gtgattgtga agagacata gaggacacat    300 gtaaggtgga aatgtaagg gcggaaagta accttatcac aaaggaatct tatccccac    360 tacttatcct tttatatttt tccgtgtcat ttttgccctt gagttttcct atataaggaa    420
ccaagttcgg catttgtgaa acaagaaaa aatttggtgt aagctatttt ctttgaagta    480
ctgaggatac aacttcagag aaatttgtaa gtttgtataa ttagttagat ctccatggag    540
tccgatgaga gtggtctccc agctatggag attgaatgca gaatcactgg cactttgaac    600
ggtgttgagt ttgaactggt gggaggtggc aagggacac ctgaacaagg gaggatgaca    660
aacaagatga agtccaccaa aggtgcattg accttctctc cgtatcttct cagccatgtc    720
```

| | |
|---|---|
| atgggttacg gtttctatca ctttggcacc tatccgagtg gctatgagaa tcccttcctt | 780 |
| catgccatca acaatggagg ttacaccaac acacgaattg agaagtatga agatggtgga | 840 |
| gtgctccacg tctccttctc ttaccgttac gaggctggga gggtcatagg agacttcaaa | 900 |
| gtgatgggaa ctggctttcc agaagattca gtcatcttca cagacaagat cattagatcc | 960 |
| aatgcaactg ttgagcatct tcacccaatg ggagacaatg acctggatgg gtcattcaca | 1020 |
| agaaccttct ctctgcgtga tggaggctac tatagctctg ttgtggactc acacatgcac | 1080 |
| ttcaaaagtg ccattcatcc tagcatcttg cagaatggtg gacccatgtt tgcctttcga | 1140 |
| agggtggaag aggatcactc aaacaccgaa cttggcatag ttgagtacca gcatgccttc | 1200 |
| aagactcctg atgcagatgc tggggaagag tgagtagtta gcttaatcac ctagagctcg | 1260 |
| aatttccccg atcgttcaaa catttggcaa taaagtttct taagattgaa tcctgttgcc | 1320 |
| ggtcttgcga tgattatcat ataatttctg ttgaattacg ttaagcatgt aataattaac | 1380 |
| atgtaatgca tgacgttatt tatgagatgg gttttatga ttagagtccc gcaattatac | 1440 |
| atttaatacg cgatagaaaa caaaatatag cgcgcaaact aggataaatt atcgcgcgcg | 1500 |
| gtgtcatcta tgttactaga tcg | 1523 |

<210> SEQ ID NO 16
<211> LENGTH: 4101
<212> TYPE: DNA
<213> ORGANISM: Artificial Sequence
<220> FEATURE:
<223> OTHER INFORMATION: Gene expression cassette of pDAB113192

<400> SEQUENCE: 16

| | |
|---|---|
| aaccttggac tcccatgttg gcaaaggcaa ccaaacaaac aatgaatgat ccgctcctgc | 60 |
| atatggggcg gtttgagtat ttcaactgcc atttgggctg aattgaagac atgctcctgt | 120 |
| cagaaattcc gtgatcttac tcaatattca gtaatctcgg ccaatatcct aaatgtgcgt | 180 |
| ggctttatct gtctttgtat tgtttcatca attcatgtaa cgtttgcttt tcttatgaat | 240 |
| tttcaaataa attatcgata gtactacgaa tatttcgtat cgctgatctt ctcaatcaca | 300 |
| atgatgcgta gtgaccccgac aaataattta agcgtcctta ataccaatcc taaaataatt | 360 |
| gaggcaaata aaattttttt gtaatttta tgatagcaga tcgattctcc agcaagcctg | 420 |
| caacaaaata ttgtgtattt ctaaatagat tttgatatta aaatcccgag aaagcaaaat | 480 |
| tgcatttaac aaaacagtaa tttagtacat taataaaaat tatgctggtg accgagctct | 540 |
| aggtgattaa gctaactact catcggtgtc caagtttgct cggaagatca cagtacttag | 600 |
| caactgccat ctcatgctgc tccacatagg tttctttgtc agcctcctta atcctctcca | 660 |
| aacgatgatc cacaaagtga acccaggca tcttgagatt cttggctggt ttcttggatc | 720 |
| gataggtagt cttgaaacta caatgcaagt agcctccacc aacgagtttc agagccattt | 780 |
| gtgaatgtcc tctcagtcca ccatcagctg ggtacaacat ctcagtgttg gcttcccacc | 840 |
| ctcttgtttt cttttgcatg acaggaccat tggacggaaa gttcacacca ttgatcttga | 900 |
| cattgtagat aatgcagcca ttctggaaag aggtatcttg agtggcagtc agaactccac | 960 |
| catcctcata ggttgttatc ctctcccatg tgaagccttc aggaaagctt tgtttgaaaa | 1020 |
| agtctggtat cccttgggtg tggttgatga atgcctttga cccatacatg aaacttgtgg | 1080 |
| caagaatgtc gaatgcaaag ggaagtggtc caccttccac aactttgatc ttcatggtct | 1140 |
| gagtgccttc atagggtttg ccttctccct cagatgtgca cttgaagtga tgattgttga | 1200 |
| ctgtgccttc catgtacaac ttcatgtgca tgttctcttt gatgagttca gacatggaga | 1260 |

-continued
tctctgttaa tcagaaaaac tcagattaat cgacaaattc gatcgcacaa actagaaact 1320
aacaccagat ctagatagaa atcacaaatc gaagagtaat tattcgacaa aactcaaatt 1380
atttgaacaa atcggatgat atttatgaaa ccctaatcga gaattaagat gatatctaac 1440
gatcaaaccc agaaaatcgt cttcgatcta agattaacag aatctaaacc aaagaacata 1500
tacgaaattg ggatcgaacg aaaacaaaat cgaagatttt gagagaataa ggaacacaga 1560
aatttacctt gatcacggta gagagaattg agagaaagtt tttaagattt tgagaaattg 1620
aaatctgaat tgtgaagaag aagctttggg tattgtttta tagaagaaga agaagaaaag 1680
acgaggacga ctaggtcacg agaaagctaa ggcggtgaag caatagctaa taataaaatg 1740
acacgtgtat tgagcgttgt ttacacgcaa agtgtcgacc tgcaggtcaa cggatcagga 1800
tattcttgtt taagatgttg aactctatgg aggtttgtat gaactgatga tctaggaccg 1860
gataagttcc cttcttcata gcgaacttat tcaaagaatg ttttgtgtat cattcttgtt 1920
acattgttat taatgaaaaa atattattgg tcattggact gaacacgagt gttaaatatg 1980
gaccaggccc caaataagat ccattgatat atgaattaaa taacaagaat aaatcgagtc 2040
accaaaccac ttgccttttt taacgagact tgttcaccaa cttgatacaa aagtcattat 2100
cctatgcaaa tcaataatca tacaaaaata tccaataaca ctaaaaaatt aaaagaaatg 2160
gataatttca caatatgtta tacgataaag aagttacttt tccaagaaat tcactgattt 2220
tataagccca cttgcattag ataaatggca aaaaaaaaca aaaaggaaaa gaaataaagc 2280
acgaagaatt ctagaaaata cgaaatacgc ttcaatgcag tgggacccac ggttcaatta 2340
ttgccaattt tcagctccac cgtatattta aaaaataaaa cgataatgct aaaaaaatat 2400
aaatcgtaac gatcgttaaa tctcaacggc tggatcttat gacgaccgtt agaaattgtg 2460
gttgtcgacg agtcagtaat aaacggcgtc aaagtggttg cagccggcac acacgagtcg 2520
tgtttatcaa ctcaaagcac aaatactttt cctcaaccta aaaataaggc aattagccaa 2580
aaacaacttt gcgtgtaaac aacgctcaat acacgtgtca ttttattatt agctattgct 2640
tcaccgcctt agctttctcg tgacctagtc gtcctcgtct tttcttcttc ttcttctata 2700
aaacaatacc caaagcttct tcttcacaat tcagatttca atttctcaaa atcttaaaaa 2760
ctttctctca attctctcta ccgtgatcaa ggtaaatttc tgtgttcctt attctctcaa 2820
aatcttcgat tttgttttcg ttcgatccca atttcgtata tgttctttgg tttagattct 2880
gttaatctta gatcgaagac gattttctgg gtttgatcgt tagatatcat cttaattctc 2940
gattagggtt tcataaatat catccgattt gttcaaataa tttgagtttt gtcgaataat 3000
tactcttcga tttgtgattt ctatctagat ctggtgttag tttctagttt gtgcgatcga 3060
atttgtcgat taatctgagt tttctgatt aacagtaatt agttagatct ccatggagtc 3120
cgatgagagt ggtctcccag ctatggagat tgaatgcaga atcactggca ctttgaacgg 3180
tgttgagttt gaactggtgg gaggtggcga agggacacct gaacaaggga ggatgacaaa 3240
caagatgaag tccaccaaag gtgcattgac cttctctccg tatcttctca gccatgtcat 3300
gggttacggt ttctatcact ttggcaccta tccgagtggc tatgagaatc cctttcttca 3360
tgccatcaac aatggaggtt acaccaacac acgaattgag aagtatgaag atggtggagt 3420
gctccacgtc tccttctctt accgttacga ggctgggagg gtcataggag acttcaaagt 3480
gatgggaact ggctttccag aagattcagt catcttcaca gacaagatca ttagatccaa 3540
tgcaactgtt gagcatcttc acccaatggg agacaatgac ctggatgggt cattcacaag 3600

| | |
|---|---|
| aaccttctct ctgcgtgatg gaggctacta tagctctgtt gtggactcac acatgcactt | 3660 |
| caaaagtgcc attcatccta gcatcttgca gaatggtgga cccatgtttg cctttcgaag | 3720 |
| ggtggaagag gatcactcaa acaccgaact tggcatagtt gagtaccagc atgccttcaa | 3780 |
| gactcctgat gcagatgctg gggaagagtg agtagttagc ttaatcacct agagctcgaa | 3840 |
| tttccccgat cgttcaaaca tttggcaata agtttcttta agattgaatc ctgttgccgg | 3900 |
| tcttgcgatg attatcatat aatttctgtt gaattacgtt aagcatgtaa taattaacat | 3960 |
| gtaatgcatg acgttattta tgagatgggt ttttatgatt agagtcccgc aattatacat | 4020 |
| ttaatacgcg atagaaaaca aaatatagcg cgcaaactag gataaattat cgcgcgcggt | 4080 |
| gtcatctatg ttactagatc g | 4101 |

<210> SEQ ID NO 17
<211> LENGTH: 4101
<212> TYPE: DNA
<213> ORGANISM: Artificial Sequence
<220> FEATURE:
<223> OTHER INFORMATION: Gene expression cassette of pDAB113193

<400> SEQUENCE: 17

| | |
|---|---|
| cgatctagta acatagatga caccgcgcgc gataatttat cctagtttgc gcgctatatt | 60 |
| ttgttttcta tcgcgtatta aatgtataat tgcgggactc taatcataaa aacccatctc | 120 |
| ataaataacg tcatgcatta catgttaatt attacatgct taacgtaatt caacagaaat | 180 |
| tatatgataa tcatcgcaag accggcaaca ggattcaatc ttaagaaact ttattgccaa | 240 |
| atgtttgaac gatcggggaa attcgagctc taggtgatta agctaactac tcactcttcc | 300 |
| ccagcatctg catcaggagt cttgaaggca tgctggtact caactatgcc aagttcggtg | 360 |
| tttgagtgat cctcttccac ccttcgaaag gcaaacatgg gtccaccatt ctgcaagatg | 420 |
| ctaggatgaa tggcactttt gaagtgcatg tgtgagtcca caacagagct atagtagcct | 480 |
| ccatcacgca gagagaaggt tcttgtgaat gacccatcca ggtcattgtc tcccattggg | 540 |
| tgaagatgct caacagttgc attggatcta atgatcttgt ctgtgaagat gactgaatct | 600 |
| tctggaaagc cagttcccat cactttgaag tctcctatga ccctcccagc ctcgtaacgg | 660 |
| taagagaagg agacgtggag cactccacca tcttcatact tctcaattcg tgtgttggtg | 720 |
| taacctccat tgttgatggc atgaagaaag ggattctcat agccactcgg ataggtgcca | 780 |
| aagtgataga accgtaacc catgacatgg ctgagaagat acggagagaa ggtcaatgca | 840 |
| cctttggtgg acttcatctt gtttgtcatc ctcccttgtt caggtgtccc ttcgccacct | 900 |
| cccaccagtt caaactcaac accgttcaaa gtgccagtga ttctgcattc aatctccata | 960 |
| gctgggagac cactctcatc ggactccatg gagatctaac taattactgt taatcagaaa | 1020 |
| aactcagatt aatcgacaaa ttcgatcgca caaactagaa actaacacca gatctagata | 1080 |
| gaaatcacaa atcgaagagt aattattcga caaaactcaa attatttgaa caaatcggat | 1140 |
| gatatttatg aaaccctaat cgagaattaa gatgatatct aacgatcaaa cccagaaaat | 1200 |
| cgtcttcgat ctaagattaa cagaatctaa accaagaac atatacgaaa ttgggatcga | 1260 |
| acgaaaacaa aatcgaagat tttgagagaa taaggaacac agaaatttac cttgatcacg | 1320 |
| gtagagagaa ttgagagaaa gttttaaga ttttgagaaa ttgaaatctg aattgtgaag | 1380 |
| aagaagcttt gggtattgtt ttatagaaga agaagaagaa aagacgagga cgactaggtc | 1440 |
| acgagaaagc taaggcggtg aagcaatagc taataataaa atgacacgtg tattgagcgt | 1500 |
| tgtttacacg caaagtgtcg acctgcaggt caacggatca ggatattctt gtttaagatg | 1560 |

```
ttgaactcta tggaggtttg tatgaactga tgatctagga ccggataagt tcccttcttc      1620
atagcgaact tattcaaaga atgttttgtg tatcattctt gttacattgt tattaatgaa      1680
aaaatattat tggtcattgg actgaacacg agtgttaaat atggaccagg ccccaaataa      1740
gatccattga tatatgaatt aaataacaag aataaatcga gtcaccaaac cacttgcctt      1800
ttttaacgag acttgttcac caacttgata caaaagtcat tatcctatgc aaatcaataa      1860
tcatacaaaa atatccaata acactaaaaa attaaaagaa atggataatt tcacaatatg      1920
ttatacgata aagaagttac ttttccaaga aattcactga ttttataagc ccacttgcat      1980
tagataaatg gcaaaaaaaa acaaaaagga aagaaataa agcacgaaga attctagaaa       2040
atacgaaata cgcttcaatg cagtgggacc cacggttcaa ttattgccaa ttttcagctc      2100
caccgtatat ttaaaaaata aaacgataat gctaaaaaaa tataaatcgt aacgatcgtt      2160
aaatctcaac ggctggatct tatgacgacc gttagaaatt gtggttgtcg acgagtcagt      2220
aataaacggc gtcaaagtgg ttgcagccgg cacacacgag tcgtgtttat caactcaaag      2280
cacaaatact tttcctcaac ctaaaaataa ggcaattagc caaaacaac tttgcgtgta       2340 aacaacgctc aatacacgtg tcattttatt attagctatt gcttcaccgc cttagctttc      2400
tcgtgaccta gtcgtcctcg tcttttcttc ttcttcttct ataaaacaat acccaaagct      2460
tcttcttcac aattcagatt tcaatttctc aaaatcttaa aaactttctc tcaattctct      2520
ctaccgtgat caaggtaaat ttctgtgttc cttattctct caaaatcttc gattttgttt      2580
tcgttcgatc ccaatttcgt atatgttctt tggtttagat tctgttaatc ttagatcgaa      2640
gacgattttc tgggtttgat cgttagatat catcttaatt ctcgattagg gtttcataaa      2700
tatcatccga tttgttcaaa taatttgagt tttgtcgaat aattactctt cgatttgtga      2760
tttctatcta gatctggtgt tagtttctag tttgtgcgat cgaatttgtc gattaatctg      2820 agttttctg attaacagag atctccatgt ctgaactcat caaagagaac atgcacatga       2880
agttgtacat ggaaggcaca gtcaacaatc atcacttcaa gtgcacatct gagggagaag      2940 gcaaaccctra tgaaggcact cagaccatga agatcaaagt tgtggaaggt ggaccacttc     3000
cctttgcatt cgacattctt gccacaagtt tcatgtatgg gtcaaaggca ttcatcaacc      3060
acacccaagg gataccagac ttttcaaac aaagctttcc tgaaggcttc acatgggaga       3120
ggataacaac ctatgaggat ggtggagttc tgactgccac tcaagatacc tctttccaga     3180
atggctgcat tatctacaat gtcaagatca atggtgtgaa cttccgtcc aatggtcctg      3240 tcatgcaaaa gaaaacaaga gggtgggaag ccaacactga tgttgtac ccagctgatg        3300 gtggactgag aggacattca caaatggctc tgaaactcgt tggtggaggc tacttgcatt     3360
gtagtttcaa gactacctat cgatccaaga accagccaa gaatctcaag atgcctgggt      3420
ttcactttgt ggatcatcgt ttggagagga ttaaggaggc tgacaaagaa acctatgtgg     3480
agcagcatga gatggcagtt gctaagtact gtgatcttcc gagcaaactt ggacaccgat     3540
gagtagttag cttaatcacc tagagctcgg tcaccagcat aattttttatt aatgtactaa    3600 attactgttt tgttaaatgc aattttgctt tctcgggatt ttaatatcaa aatctattta    3660
gaaatacaca atattttgtt gcaggcttgc tggagaatcg atctgctatc ataaaaatta    3720
caaaaaaatt ttatttgcct caattatttt aggattggta ttaaggacgc ttaaattatt    3780
tgtcgggtca ctacgcatca ttgtgattga gaagatcagc gatacgaaat attcgtagta    3840
ctatcgataa tttatttgaa aattcataag aaaagcaaac gttacatgaa ttgatgaaac    3900
```

-continued

```
aatacaaaga cagataaagc cacgcacatt taggatattg gccgagatta ctgaatattg    3960
agtaagatca cggaatttct gacaggagca tgtcttcaat tcagcccaaa tggcagttga    4020
aatactcaaa ccgccccata tgcaggagcg gatcattcat tgtttgtttg gttgcctttg    4080
ccaacatggg agtccaaggt t                                              4101

<210> SEQ ID NO 18
<211> LENGTH: 3797
<212> TYPE: DNA
<213> ORGANISM: Artificial Sequence
<220> FEATURE:
<223> OTHER INFORMATION: Gene expression cassette of pDAB113194

<400> SEQUENCE: 18
aaccttggac tcccatgttg gcaaaggcaa ccaaacaaac aatgaatgat ccgctcctgc      60
atatggggcg gtttgagtat ttcaactgcc atttgggctg aattgaagac atgctcctgt     120
cagaaattcc gtgatcttac tcaatattca gtaatctcgg ccaatatcct aaatgtgcgt     180
ggctttatct gtctttgtat tgtttcatca attcatgtaa cgtttgcttt tcttatgaat     240
tttcaaataa attatcgata gtactacgaa tatttcgtat cgctgatctt ctcaatcaca     300
atgatgcgta gtgacccgac aaataattta agcgtcctta ataccaatcc taaataatt      360 gaggcaaata aaatttttt gtaatttta tgatagcaga tcgattctcc agcaagcctg      420
caacaaaata ttgtgtattt ctaaatagat tttgatatta aatcccgag aaagcaaat      480 tgcatttaac aaaacagtaa tttagtacat taataaaaat tatgctggtg accgagctct     540
aggtgattaa gctaactact catcggtgtc caagtttgct cggaagatca cagtacttag     600
caactgccat ctcatgctgc tccacatagg tttctttgtc agcctcctta atcctctcca     660
aacgatgatc cacaaagtga aacccaggca tcttgagatt cttggctggt ttcttggatc     720
gataggtagt cttgaaacta caatgcaagt agcctccacc aacgagtttc agagccattt     780
gtgaatgtcc tctcagtcca ccatcagctg gtacaacat ctcagtgttg gcttcccacc      840
ctcttgtttt cttttgcatg acaggaccat tggacggaaa gttcacacca ttgatcttga     900
cattgtagat aatgcagcca ttctggaaag aggtatcttg agtggcagtc agaactccac     960
catcctcata ggttgttatc ctctcccatg tgaagccttc aggaaagctt tgtttgaaaa    1020
agtctggtat cccttgggtg tggttgatga atgcctttga cccatacatg aaacttgtgg    1080
caagaatgtc gaatgcaaag ggaagtggtc caccttccac aactttgatc ttcatggtct    1140
gagtgccttc atagggtttg ccttctccct cagatgtgca cttgaagtga tgattgttga    1200
ctgtgccttc catgtacaac ttcatgtgca tgttctcttt gatgagttca gacatggaga    1260
tctaactaat tatacaaact acaaatttc tctgaagttg tatcctcagt acttcaaaga     1320
aaatagctta caccaaattt tttcttgttt tcacaaatgc cgaacttggt tccttatata    1380
ggaaaactca aggcaaaaa tgacacggaa aaatataaaa ggataagtag tggggataa     1440 gattcctttg tgataaggtt actttccgcg tcgacctgca ggtcaacgga tcaggatatt    1500
cttgtttaag atgttgaact ctatggaggt ttgtatgaac tgatgatcta ggaccggata    1560
agttcccttc ttcatagcga acttattcaa agaatgtttt gtgtatcatt cttgttacat    1620
tgttattaat gaaaaatat tattggtcat tggactgaac acgagtgtta aatatggacc     1680 aggcccaaa taagatccat tgatatatga attaaataac aagaataaat cgagtcacca    1740
aaccacttgc ctttttaac gagacttgtt caccaacttg atacaaaagt cattatccta    1800
tgcaaatcaa taatcataca aaatatcca ataacactaa aaaattaaaa gaaatggata    1860
```

```
atttcacaat atgttatacg ataaagaagt tacttttcca agaaattcac tgattttata    1920
agcccacttg cattagataa atggcaaaaa aaaacaaaaa ggaaaagaaa taaagcacga    1980
agaattctag aaaatacgaa atacgcttca atgcagtggg acccacggtt caattattgc    2040
caattttcag ctccaccgta tatttaaaaa ataaaacgat aatgctaaaa aaatataaat    2100
cgtaacgatc gttaaatctc aacggctgga tcttatgacg accgttagaa attgtggttg    2160
tcgacgagtc agtaataaac ggcgtcaaag tggttgcagc cggcacacac gagtcgtgtt    2220
tatcaactca aagcacaaat acttttcctc aacctaaaaa taaggcaatt agccaaaaac    2280
aactttgcgt gtaaacaacg ctcaatacac gtgtcatttt attattagct attgcttcac    2340
cgccttagct ttctcgtgac ctagtcgtcc tcgtcttttc ttcttcttct tctataaaac    2400
aatacccaaa gcttcttctt cacaattcag atttcaattt ctcaaaatct taaaaacttt    2460
ctctcaattc tctctaccgt gatcaaggta aatttctgtg ttccttattc tctcaaaatc    2520
ttcgattttg ttttcgttcg atcccaattt cgtatatgtt ctttggttta gattctgtta    2580
atcttagatc gaagacgatt ttctgggttt gatcgttaga tatcatctta attctcgatt    2640
agggtttcat aaatatcatc cgatttgttc aaataatttg agttttgtcg aataattact    2700
cttcgatttg tgatttctat ctagatctgg tgttagtttc tagtttgtgc gatcgaattt    2760
gtcgattaat ctgagttttt ctgattaaca gtaattagtt agatctccat ggagtccgat    2820
gagagtggtc tcccagctat ggagattgaa tgcagaatca ctggcacttt gaacggtgtt    2880
gagtttgaac tggtgggagg tggcgaaggg acacctgaac aagggaggat gacaaacaag    2940
atgaagtcca ccaaaggtgc attgaccttc tctccgtatc ttctcagcca tgtcatgggt    3000
tacggtttct atcactttgg cacctatccg agtggctatg agaatccctt tcttcatgcc    3060
atcaacaatg gaggttacac caacacacga attgagaagt atgaagatgg tggagtgctc    3120
cacgtctcct tctcttaccg ttacgaggct gggagggtca taggagactt caaagtgatg    3180
ggaactggct ttccagaaga ttcagtcatc ttcacagaca agatcattag atccaatgca    3240
actgttgagc atcttcaccc aatgggagac aatgacctgg atgggtcatt cacaagaacc    3300
ttctctctgc gtgatggagg ctactatagc tctgttgtgg actcacacat gcacttcaaa    3360
agtgccattc atcctagcat cttgcagaat ggtggaccca tgtttgcctt tcgaagggtg    3420
gaagaggatc actcaaacac cgaacttggc atagttgagt accagcatgc cttcaagact    3480
cctgatgcag atgctgggga agagtgagta gttagcttaa tcacctagag ctcgaatttc    3540
cccgatcgtt caaacatttg gcaataaagt ttcttaagat tgaatcctgt tgccggtctt    3600
gcgatgatta tcatataatt tctgttgaat tacgttaagc atgtaataat taacatgtaa    3660
tgcatgacgt tatttatgag atgggttttt atgattagag tcccgcaatt atacatttaa    3720
tacgcgatag aaaacaaaat atagcgcgca aactaggata aattatcgcg cgcggtgtca    3780
tctatgttac tagatcg                                                 3797
```

<210> SEQ ID NO 19
<211> LENGTH: 3788
<212> TYPE: DNA
<213> ORGANISM: Artificial Sequence
<220> FEATURE:
<223> OTHER INFORMATION: Gene expression cassette of pDAB113195

<400> SEQUENCE: 19

```
cgatctagta acatagatga caccgcgcgc gataatttat cctagtttgc gcgctatatt      60
```

```
ttgttttcta tcgcgtatta aatgtataat tgcgggactc taatcataaa aacccatctc    120
ataaataacg tcatgcatta catgttaatt attacatgct taacgtaatt caacagaaat    180
tatatgataa tcatcgcaag accggcaaca ggattcaatc ttaagaaact ttattgccaa    240
atgtttgaac gatcggggaa attcgagctc taggtgatta agctaactac tcactcttcc    300
ccagcatctg catcaggagt cttgaaggca tgctggtact caactatgcc aagttcggtg    360
tttgagtgat cctcttccac ccttcgaaag gcaaacatgg gtccaccatt ctgcaagatg    420
ctaggatgaa tggcactttt gaagtgcatg tgtgagtcca acagagct atagtagcct    480 ccatcacgca gagagaaggt tcttgtgaat gacccatcca ggtcattgtc tcccattggg    540
tgaagatgct caacagttgc attggatcta atgatcttgt ctgtgaagat gactgaatct    600
tctggaaagc cagttcccat cactttgaag tctcctatga ccctcccagc ctcgtaacgg    660
taagagaagg agacgtggag cactccacca tcttcatact tctcaattcg tgtgttggtg    720
taacctccat tgttgatggc atgaagaaag ggattctcat agccactcgg ataggtgcca    780
aagtgataga accgtaacc catgacatgg ctgagaagat acgagagaa ggtcaatgca    840 cctttggtgg acttcatctt gtttgtcatc ctcccttgtt caggtgtccc ttcgccacct    900
cccaccagtt caaactcaac accgttcaaa gtgccagtga ttctgcattc aatctccata    960
gctgggagac cactctcatc ggactccatg gagatctaac taattataca aacttacaaa   1020
tttctctgaa gttgtatcct cagtacttca aagaaaatag cttacaccaa attttttctt   1080
gttttcacaa atgccgaact tggttcctta tataggaaaa ctcaagggca aaaatgacac   1140 ggaaaatat aaaaggataa gtagtggggg ataagattcc tttgtgataa ggttactttc    1200
cgcgtcgacc tgcaggtcaa cggatcagga tattcttgtt taagatgttg aactctatgg   1260
aggtttgtat gaactgatga tctaggaccg gataagttcc cttcttcata gcgaacttat   1320
tcaaagaatg ttttgtgtat cattcttgtt acattgttat taatgaaaaa atattattgg   1380
tcattggact gaacacgagt gttaaatatg gaccaggccc caaataagat ccattgatat   1440
atgaattaaa taacaagaat aaatcgagtc accaaaccac ttgcctttt taacgagact   1500 tgttcaccaa cttgatacaa aagtcattat cctatgcaaa tcataatca tacaaaaata    1560 tccaataaca ctaaaaaatt aaaagaaatg gataatttca caatatgtta tacgataaag   1620
aagttacttt tccaagaaat tcactgattt tataagccca cttgcattag ataaatggca   1680
aaaaaaaaca aaaaggaaaa gaaataaagc acgaagaatt ctagaaaata cgaaatacgc   1740
ttcaatgcag tgggacccac ggttcaatta ttgccaattt tcagctccac cgtatattta   1800
aaaaataaaa cgataatgct aaaaaaatat aaatcgtaac gatcgttaaa tctcaacggc   1860
tggatcttat gacgaccgtt agaaattgtg gttgtcgacg agtcagtaat aaacggcgtc   1920
aaagtggttg cagccggcac acacgagtcg tgtttatcaa ctcaaagcac aaatactttt   1980
cctcaaccta aaataaggc aattagccaa aacaactttt gcgtgtaaac aacgctcaat    2040
acacgtgtca ttttattatt agctattgct tcaccgcctt agctttctcg tgacctagtc   2100
gtcctcgtct tttcttcttc ttcttctata aaacaatacc caaagcttct tcttcacaat   2160
tcagatttca atttctcaaa atcttaaaaa ctttctctca attctctcta ccgtgatcaa   2220
ggtaaatttc tgtgttcctt attctctcaa aatcttcgat tttgttttcg ttcgatccca   2280
atttcgtata tgttctttgg tttagattct gttaatctta gatcgaagac gattttctgg   2340
gtttgatcgt tagatatcat cttaattctc gattagggtt tcataaatat catccgattt   2400
gttcaaataa tttgagtttt gtcgaataat tactcttcga tttgtgattt ctatctagat   2460
```

```
ctggtgttag tttctagttt gtgcgatcga atttgtcgat taatctgagt ttttctgatt      2520
aacagagatc tccatgtctg aactcatcaa agagaacatg cacatgaagt tgtacatgga      2580
aggcacagtc aacaatcatc acttcaagtg cacatctgag ggagaaggca aaccctatga      2640
aggcactcag accatgaaga tcaaagttgt ggaaggtgga ccacttccct ttgcattcga      2700
cattcttgcc acaagtttca tgtatgggtc aaaggcattc atcaaccaca cccaagggat      2760
accagacttt tcaaacaaa gctttcctga aggcttcaca tgggagagga taacaaccta      2820
tgaggatggt ggagttctga ctgccactca agatacctct ttccagaatg ctgcattat       2880 ctacaatgtc aagatcaatg gtgtgaactt ccgtccaat ggtcctgtca tgcaaaagaa       2940
aacaagaggg tgggaagcca acactgagat gttgtaccca gctgatggtg gactgagagg      3000
acattcacaa atggctctga aactcgttgg tggaggctac ttgcattgta gtttcaagac      3060
tacctatcga tccaagaaac cagccaagaa tctcaagatg cctgggtttc actttgtgga     3120
tcatcgtttg gagaggatta aggaggctga caaagaaacc tatgtggagc agcatgagat     3180
ggcagttgct aagtactgtg atcttccgag caaacttgga caccgatgag tagttagctt     3240
aatcacctag agctcggtca ccagcataat ttttattaat gtactaaatt actgttttgt     3300
taaatgcaat tttgctttct cgggatttta atatcaaaat ctatttagaa atacacaata     3360
ttttgttgca ggcttgctgg agaatcgatc tgctatcata aaaattacaa aaaaatttta    3420
tttgcctcaa ttatttttagg attggtatta aggacgctta aattatttgt cgggtcacta    3480
cgcatcattg tgattgagaa gatcagcgat acgaaatatt cgtagtacta tcgataattt     3540
atttgaaaat tcataagaaa agcaaacgtt acatgaattg atgaaacaat acaaagacag     3600
ataaagccac gcacatttag gatattggcc gagattactg aatattgagt aagatcacgg     3660
aatttctgac aggagcatgt cttcaattca gcccaaatgg cagttgaaat actcaaaccg     3720
ccccatatgc aggagcggat cattcattgt ttgtttggtt gcctttgcca acatgggagt     3780
ccaaggtt                                                              3788
```

<210> SEQ ID NO 20
<211> LENGTH: 3296
<212> TYPE: DNA
<213> ORGANISM: Artificial Sequence
<220> FEATURE:
<223> OTHER INFORMATION: Gene expression cassette of pDAB113196

<400> SEQUENCE: 20

```
aaccttggac tccatgttg gcaaaggcaa ccaaacaaac aatgaatgat ccgctcctgc       60
atatggggcg gtttgagtat ttcaactgcc atttgggctg aattgaagac atgctcctgt     120
cagaaattcc gtgatcttac tcaatattca gtaatctcgg ccaatatcct aaatgtgcgt    180
ggctttatct gtctttgtat tgtttcatca attcatgtaa cgtttgcttt tcttatgaat     240
tttcaaataa attatcgata gtactacgaa tatttcgtat cgctgatctt ctcaatcaca     300
atgatgcgta gtgacccgac aaataattta agcgtcctta ataccaatcc taaaataatt     360
gaggcaaata aaattttttt gtaatttttta tgatagcaga tcgattctcc agcaagcctg    420
caacaaaata ttgtgtattt ctaaatagat tttgatatta aatcccgag aaagcaaaat     480 tgcatttaac aaaacagtaa tttagtacat taataaaaat tatgctggtg accgagctct     540
aggtgattaa gctaactact catccggtgtc caagtttgct cggaagatca cagtacttag    600
caactgccat ctcatgctgc tccacatagg tttctttgtc agcctcctta atcctctcca     660
```

```
aacgatgatc cacaaagtga aacccaggca tcttgagatt cttggctggt ttcttggatc      720
gataggtagt cttgaaacta caatgcaagt agcctccacc aacgagtttc agagccattt      780
gtgaatgtcc tctcagtcca ccatcagctg gtacaacat  ctcagtgttg gcttcccacc      840
ctcttgtttt cttttgcatg acaggaccat tggacgaaaa gttcacacca ttgatcttga      900
cattgtagat aatgcagcca ttctggaaag aggtatcttg agtggcagtc agaactccac      960
catcctcata ggttgttatc ctctcccatg tgaagccttc aggaaagctt tgtttgaaaa     1020
agtctggtat cccttgggtg tggttgatga atgcctttga cccatacatg aaacttgtgg     1080
caagaatgtc gaatgcaaag ggaagtggtc caccttccac aactttgatc ttcatggtct     1140
gagtgccttc atagggtttg ccttctccct cagatgtgca cttgaagtga tgattgttga     1200
ctgtgccttc catgtacaac ttcatgtgca tgttctcttt gatgagttca gacatggaga     1260
tctctgttaa tcagaaaaac tcagattaat cgacaaattc gatcgcacaa actagaaact     1320
aacaccagat ctagatagaa atcacaaatc gaagagtaat tattcgacaa aactcaaatt     1380
atttgaacaa atcggatgat atttatgaaa ccctaatcga gaattaagat gatatctaac     1440
gatcaaaccc agaaaatcgt cttcgatcta agattaacag aatctaaacc aaagaacata     1500
tacgaaattg ggatcgaacg aaaacaaaat cgaagatttt gagagaataa ggaacacaga     1560
aatttacctt gatcacggta gagagaattg agagaaagtt tttaagattt tgagaaattg     1620
aaatctgaat tgtgaagaag aagctttggg tattgtttta tagaagaaga agaagaaaag     1680
acgaggacga ctaggtcacg agaaagctaa ggcggtgaag caatagctaa taataaaatg     1740
acacgtgtat tgagcgttgt ttacacgcaa agtccagaag gtaattatcc aagatgtagc     1800
atcaagaatc caatgtttac gggaaaaact atggaagtat tatgtgagct cagcaagaag     1860
cagatcaata tgcggcacat atgcaaccta tgttcaaaaa tgaagaatgt acagatacaa     1920
gatcctatac tgccagaata cgaagaagaa tacgtagaaa ttgaaaaaga gaaccaggc      1980 gaagaaaaga atcttgaaga cgtaagcact gacgacaaca atgaaaagaa gaagataagg     2040
tcggtgattg tgaaagagac atagaggaca catgtaaggt ggaaaatgta agggcggaaa     2100
gtaaccttat cacaaaggaa tcttatcccc cactacttat cctttatat  ttttccgtgt     2160 cattttttgcc cttgagtttt cctatataag gaaccaagtt cggcatttgt gaaaacaaga     2220
aaaaatttgg tgtaagctat tttctttgaa gtactgagga tacaacttca gagaaatttg     2280
taagtttgta taattagtta gatctccatg gagtccgatg agagtggtct cccagctatg     2340
gagattgaat gcagaatcac tggcacttg  aacggtgttg agtttgaact ggtgggaggt     2400
ggcgaaggga cacctgaaca agggaggatg acaaacaaga tgaagtccac caaaggtgca     2460
ttgaccttct ctccgtatct tctcagccat gtcatgggtt acggtttcta tcactttggc     2520
acctatccga gtggctatga gaatcccttt cttcatgcca tcaacaatgg aggttacacc     2580
aacacacgaa ttgagaagta tgaagatggt ggagtgctcc acgtctcctt ctcttaccgt     2640
tacgaggctg ggagggtcat aggagacttc aaagtgatgg gaactggctt tccagaagat     2700
tcagtcatct tcacagacaa gatcattaga tccaatgcaa ctgttgagca tcttcaccca     2760
atgggagaca atgacctgga tggtcattc  acaagaacct tctctctgcg tgatggaggc     2820
tactatagct ctgttgtgga ctcacacatg cacttcaaaa gtgccattca tcctagcatc     2880
ttgcagaatg gtggacccat gttttgccttt cgaagggtgg aagaggatca ctcaaacacc     2940
gaacttggca tagttgagta ccagcatgcc ttcaagactc ctgatgcaga tgctggggaa     3000
gagtgagtag ttagcttaat cacctagagc tcgaatttcc ccgatcgttc aaacatttgg     3060
```

```
caataaagtt tcttaagatt gaatcctgtt gccggtcttg cgatgattat catataattt    3120
ctgttgaatt acgttaagca tgtaataatt aacatgtaat gcatgacgtt atttatgaga    3180
tgggttttta tgattagagt cccgcaatta tacatttaat acgcgataga aaacaaaata    3240
tagcgcgcaa actaggataa attatcgcgc gcggtgtcat ctatgttact agatcg        3296
```

<210> SEQ ID NO 21
<211> LENGTH: 3305
<212> TYPE: DNA
<213> ORGANISM: Artificial Sequence
<220> FEATURE:
<223> OTHER INFORMATION: Gene expression cassette of pDAB113197

<400> SEQUENCE: 21

```
cgatctagta acatagatga caccgcgcgc gataatttat cctagtttgc gcgctatatt      60
ttgttttcta tcgcgtatta atgtataat tgcgggactc taatcataaa acccatctc     120 ataaataacg tcatgcatta catgttaatt attacatgct taacgtaatt caacagaaat    180
tatatgataa tcatcgcaag accggcaaca ggattcaatc ttaagaaact ttattgccaa    240
atgtttgaac gatcggggaa attcgagctc taggtgatta agctaactac tcactcttcc    300
ccagcatctg catcaggagt cttgaaggca tgctggtact caactatgcc aagttcggtg    360
tttgagtgat cctcttccac ccttcgaaag gcaaacatgg gtccaccatt ctgcaagatg    420
ctaggatgaa tggcactttt gaagtgcatg tgtgagtcca acagagct atagtagcct    480 ccatcacgca gagagaaggt tcttgtgaat gacccatcca ggtcattgtc tcccattggg    540
tgaagatgct caacagttgc attggatcta atgatcttgt ctgtgaagat gactgaatct    600
tctggaaagc cagttcccat cactttgaag tctcctatga ccctcccagc ctcgtaacgg    660
taagagaagg agacgtggag cactccacca tcttcatact tctcaattcg tgtgttggtg    720
taacctccat tgttgatggc atgaagaaag ggattctcat agccactcgg ataggtgcca    780
aagtgataga aaccgtaacc catgacatgg ctgagaagat acggagagaa ggtcaatgca    840
cctttggtgg acttcatctt gtttgtcatc ctcccttgtt caggtgtccc ttcgccacct    900
cccaccagtt caaactcaac accgttcaaa gtgccagtga ttctgcattc aatctccata    960
gctgggagac cactctcatc ggactccatg gagatctaac taattactgt taatcagaaa   1020
aactcagatt aatcgacaaa ttcgatcgca caaactagaa actaacacca gatctagata   1080
gaaatcacaa atcgaagagt aattattcga caaaactcaa attatttgaa caaatcggat   1140
gatatttatg aaaccctaat cgagaattaa gatgatatct aacgatcaaa cccagaaaat   1200
cgtcttcgat ctaagattaa cagaatctaa accaagaac atatacgaaa ttgggatcga   1260
acgaaaacaa atcgaagat tttgagagaa taaggaacac agaaatttac cttgatcacg    1320
gtagagagaa ttgagagaaa gtttttaaga ttttgagaaa ttgaaatctg aattgtgaag    1380
aagaagcttt gggtattgtt ttatagaaga agaagaagaa aagacgagga cgactaggtc    1440
acgagaaagc taaggcggtg aagcaatagc taataataaa atgacacgtg tattgagcgt    1500
tgtttacacg caaagtccag aaggtaatta tccaagatgt agcatcaaga atccaatgtt    1560
tacgggaaaa actatggaag tattatgtga gctcagcaag aagcagatca atatgcggca    1620
catatgcaac ctatgttcaa aaatgaagaa tgtacagata caagatccta tactgccaga    1680
atacgaagaa gaatacgtag aaattgaaaa agaagaacca ggcgaagaaa agaatcttga    1740
agacgtaagc actgacgaca acaatgaaaa gaagaagata aggtcggtga ttgtgaaaga    1800
```

```
gacatagagg acacatgtaa ggtggaaaat gtaagggcgg aaagtaacct tatcacaaag      1860
gaatcttatc ccccactact tatccttta tatttttccg tgtcatttt gcccttgagt        1920 tttcctatat aaggaaccaa gttcggcatt tgtgaaaaca agaaaaaatt tggtgtaagc      1980
tattttcttt gaagtactga ggatacaact tcagagaaat ttgtaagttt gtataattag     2040
ttagatctcc atgtctgaac tcatcaaaga gaacatgcac atgaagttgt acatggaagg     2100
cacagtcaac aatcatcact tcaagtgcac atctgaggga gaaggcaaac cctatgaagg     2160
cactcagacc atgaagatca agttgtgga aggtggacca cttccctttg cattcgacat      2220
tcttgccaca agtttcatgt atgggtcaaa ggcattcatc aaccacaccc aagggatacc     2280
agactttttc aaacaaagct ttcctgaagg cttcacatgg gagaggataa caacctatga     2340
ggatggtgga gttctgactg ccactcaaga tacctctttc cagaatggct gcattatcta     2400
caatgtcaag atcaatggtg tgaactttcc gtccaatggt cctgtcatgc aaaagaaaac     2460
aagagggtgg gaagccaaca ctgagatgtt gtacccagct gatggtggac tgagaggaca     2520
ttcacaaatg gctctgaaac tcgttggtgg aggctacttg cattgtagtt tcaagactac     2580
ctatcgatcc aagaaaccag ccaagaatct caagatgcct gggtttcact tgtggatca     2640 tcgtttggag aggattaagg aggctgacaa agaaacctat gtggagcagc atgagatggc     2700
agttgctaag tactgtgatc ttccgagcaa acttggacac cgatgagtag ttagcttaat     2760
cacctagagc tcggtcacca gcataatttt tattaatgta ctaaattact gttttgttaa     2820 atgcaattt gctttctcgg gatttaata tcaaatcta tttagaaata cacaatatt       2880 tgttgcaggc ttgctggaga atcgatctgc tatcataaaa attacaaaaa aattttattt     2940
gcctcaatta ttttaggatt ggtattaagg acgcttaaat tatttgtcgg gtcactacgc     3000
atcattgtga ttgagaagat cagcgatacg aaatattcgt agtactatcg ataatttatt    3060
tgaaaattca taagaaaagc aaacgttaca tgaattgatg aaacaataca aagacagata    3120
aagccacgca catttaggat attggccgag attactgaat attgagtaag atcacggaat    3180
ttctgacagg agcatgtctt caattcagcc caaatggcag ttgaaatact caaaccgccc    3240
catatgcagg agcggatcat tcattgtttg tttggttgcc tttgccaaca tgggagtcca    3300
aggtt                                                                  3305
```

<210> SEQ ID NO 22
<211> LENGTH: 2992
<212> TYPE: DNA
<213> ORGANISM: Artificial Sequence
<220> FEATURE:
<223> OTHER INFORMATION: Gene expression cassette of pDAB113198

<400> SEQUENCE: 22

```
aaccttggac tccatgttg gcaaaggcaa ccaaacaaac aatgaatgat ccgctcctgc         60
atatggggcg gtttgagtat ttcaactgcc atttgggctg aattgaagac atgctcctgt       120
cagaaattcc gtgatcttac tcaatattca gtaatctcgg ccaatatcct aaatgtgcgt       180
ggctttatct gtctttgtat tgtttcatca attcatgtaa cgtttgcttt tcttatgaat       240
tttcaaataa attatcgata gtactacgaa tatttcgtat cgctgatctt ctcaatcaca       300
atgatgcgta gtgacccgac aaataattta agcgtcctta taccaatcc taaaataatt        360 gaggcaaata aaatttttt gtaatttta tgatagcaga tcgattctcc agcaagcctg         420
caacaaaata ttgtgtattt ctaaatagat tttgatatta aatcccgag aaagcaaaat       480 tgcatttaac aaaacagtaa tttagtacat taataaaaat tatgctggtg accgagctct      540
```

```
aggtgattaa gctaactact catcggtgtc caagtttgct cggaagatca cagtacttag      600
caactgccat ctcatgctgc tccacatagg tttctttgtc agcctcctta atcctctcca      660
aacgatgatc cacaaagtga aacccaggca tcttgagatt cttggctggt ttcttggatc      720
gataggtagt cttgaaacta caatgcaagt agcctccacc aacgagtttc agagccattt      780
gtgaatgtcc tctcagtcca ccatcagctg gtacaacat ctcagtgttg cttcccacc        840 ctcttgtttt cttttgcatg acaggaccat tggacggaaa gttcacacca ttgatcttga      900
cattgtagat aatgcagcca ttctggaaag aggtatcttg agtggcagtc agaactccac      960
catcctcata ggttgttatc ctctcccatg tgaagccttc aggaaagctt tgtttgaaaa     1020
agtctggtat cccttgggtg tggttgatga atgcctttga cccatacatg aaacttgtgg     1080
caagaatgtc gaatgcaaag ggaagtggtc caccttccac aactttgatc ttcatggtct     1140
gagtgccttc atagggtttg ccttctccct cagatgtgca cttgaagtga tgattgttga     1200
ctgtgccttc catgtacaac ttcatgtgca tgttctcttt gatgagttca gacatggaga     1260
tctaactaat tatacaaact tacaaatttc tctgaagttg tatcctcagt acttcaaaga     1320
aaatagctta caccaaattt tttcttgttt tcacaaatgc cgaacttggt tccttatata     1380
ggaaaactca agggcaaaaa tgacacggaa aaatataaaa ggataagtag tgggggataa     1440
gattcctttg tgataaggtt actttccgcc cagaaggtaa ttatccaaga tgtagcatca     1500
agaatccaat gtttacggga aaaactatgg aagtattatg tgagctcagc aagaagcaga     1560
tcaatatgcg gcacatatgc aacctatgtt caaaaatgaa gaatgtacag atacaagatc     1620
ctatactgcc agaatacgaa gaagaatacg tagaaattga aaagaagaa ccaggcgaag      1680 aaaagaatct tgaagacgta agcactgacg acaacaatga aaagaagaag ataaggtcgg     1740
tgattgtgaa agagacatag aggacacatg taaggtggaa aatgtaaggg cggaaagtaa     1800
ccttatcaca aaggaatctt atcccccact acttatcctt ttatattttt ccgtgtcatt     1860
tttgcccttg agttttccta tataaggaac caagttcggc atttgtgaaa acaagaaaaa     1920
atttggtgta agctattttc tttgaagtac tgaggataca acttcagaga aatttgtaag     1980
tttgtataat tagttagatc tccatggagt ccgatgagag tggtctccca gctatggaga     2040
ttgaatgcag aatcactggc actttgaacg gtgttgagtt tgaactggtg ggaggtggcg     2100
aagggacacc tgaacaaggg aggatgacaa acaagatgaa gtccaccaaa ggtgcattga     2160
ccttctctcc gtatcttctc agccatgtca tgggttacgg tttctatcac tttggcacct     2220
atccgagtgg ctatgagaat ccctttcttc atgccatcaa caatggaggt tacaccaaca     2280
cacgaattga gaagtatgaa gatggtggag tgctccacgt ctccttctct taccgttacg     2340
aggctgggag ggtcatagga gacttcaaag tgatgggaac tggctttcca gaagattcag     2400
tcatcttcac agacaagatc attagatcca atgcaactgt tgagcatctt cacccaatgg     2460
gagacaatga cctggatggg tcattcacaa gaaccttctc tctgcgtgat ggaggctact     2520
atagctctgt tgtggactca cacatgcact tcaaaagtgc cattcatcct agcatcttgc     2580
agaatggtgg acccatgttt gccttttcgaa gggtggaaga ggatcactca aacaccgaac     2640
ttggcatagt tgagtaccag catgccttca agactcctga tgcagatgct ggggaagagt     2700
gagtagttag cttaatcacc tagagctcga atttccccga tcgttcaaac atttggcaat     2760
aaagtttctt aagattgaat cctgttgccg gtcttgcgat gattatcata taatttctgt     2820
tgaattacgt taagcatgta ataattaaca tgtaatgcat gacgttattt atgagatggg     2880
```

```
ttttatgat tagagtcccg caattataca tttaatacgc gatagaaaac aaaatatagc    2940
gcgcaaacta ggataaatta tcgcgcgcgg tgtcatctat gttactagat cg           2992

<210> SEQ ID NO 23
<211> LENGTH: 2992
<212> TYPE: DNA
<213> ORGANISM: Artificial Sequence
<220> FEATURE:
<223> OTHER INFORMATION: Gene expression cassette of pDAB113199

<400> SEQUENCE: 23
cgatctagta acatagatga caccgcgcgc gataatttat cctagtttgc gcgctatatt     60
ttgttttcta tcgcgtatta atgtataat tgcgggactc taatcataaa aacccatctc    120
ataaataacg tcatgcatta catgttaatt attacatgct taacgtaatt caacagaaat    180
tatatgataa tcatcgcaag accggcaaca ggattcaatc ttaagaaact ttattgccaa    240
atgtttgaac gatcggggaa attcgagctc taggtgatta agctaactac tcactcttcc    300
ccagcatctg catcaggagt cttgaaggca tgctggtact caactatgcc aagttcggtg    360
tttgagtgat cctcttccac ccttcgaaag gcaaacatgg gtccaccatt ctgcaagatg    420
ctaggatgaa tggcactttt gaagtgcatg tgtgagtcca aacagagct atagtagcct     480 ccatcacgca gagagaaggt tcttgtgaat gacccatcca ggtcattgtc tcccattggg    540
tgaagatgct aacagttgc attggatcta atgatcttgt ctgtgaagat gactgaatct     600
tctggaaagc cagttcccat cactttgaag tctcctatga ccctcccagc ctcgtaacgg    660
taagagaagg agacgtggag cactccacca tcttcatact tctcaattcg tgtgttggtg    720
taacctccat tgttgatggc atgaagaaag ggattctcat agccactcgg ataggtgcca    780
aagtgataga aaccgtaacc catgacatgg ctgagaagat acggagagaa ggtcaatgca    840
cctttggtgg acttcatctt gtttgtcatc ctcccttgtt caggtgtccc ttcgccacct    900
cccaccagtt caaactcaac accgttcaaa gtgccagtga ttctgcattc aatctccata    960
gctgggagac cactctcatc ggactccatg gagatctaac taattataca aacttacaaa   1020
tttctctgaa gttgtatcct cagtacttca aagaaaatag cttacaccaa attttttctt   1080
gttttcacaa atgccgaact tggttcctta tataggaaaa ctcaagggca aaaatgacac   1140
ggaaaaatat aaaaggataa gtagtggggg ataagattcc tttgtgataa ggttactttc   1200
cgcccagaag gtaattatcc aagatgtagc atcaagaatc caatgtttac gggaaaaact   1260
atggaagtat tatgtgagct cagcaagaag cagatcaata tgcggcacat atgcaaccta   1320
tgttcaaaaa tgaagaatgt acagatacaa gatcctatac tgccagaata cgaagaagaa   1380
tacgtagaaa ttgaaaaaga gaaccaggc gaagaaaaga atcttgaaga cgtaagcact    1440
gacgacaaca atgaaaagaa gaagataagg tcggtgattg tgaaagagac atagaggaca   1500
catgtaaggt ggaaaatgta agggcggaaa gtaaccttat cacaaaggaa tcttatcccc   1560
cactacttat cctttatat ttttccgtgt cattttgcc cttgagtttt cctatataag    1620
gaaccaagtt cggcatttgt gaaaacaaga aaaatttgg tgtaagctat tttctttgaa   1680
gtactgagga tacaacttca gagaaatttg taagtttgta taattagtta gatctccatg   1740
tctgaactca tcaaagagaa catgcacatg aagttgtaca tggaaggcac agtcaacaat   1800
catcacttca gtgcacatc tgagggagaa ggcaaaccct atgaaggcac tcagaccatg    1860
aagatcaaag ttgtgaagg tggaccactt ccctttgcat tcgacattct tgccacaagt   1920
ttcatgtatg ggtcaaaggc attcatcaac cacacccaag ggataccaga cttttcaaa    1980
```

```
caaagctttc ctgaaggctt cacatgggag aggataacaa cctatgagga tggtggagtt    2040
ctgactgcca ctcaagatac ctctttccag aatggctgca ttatctacaa tgtcaagatc    2100
aatggtgtga actttccgtc caatggtcct gtcatgcaaa agaaaacaag agggtgggaa    2160
gccaacactg agatgttgta cccagctgat ggtggactga gaggacattc acaaatggct    2220
ctgaaactcg ttggtggagg ctacttgcat tgtagtttca agactaccta tcgatccaag    2280
aaaccagcca agaatctcaa gatgcctggg tttcactttg tggatcatcg tttggagagg    2340
attaaggagg ctgacaaaga aacctatgtg gagcagcatg agatggcagt tgctaagtac    2400
tgtgatcttc cgagcaaact tggacaccga tgagtagtta gcttaatcac ctagagctcg    2460
gtcaccagca taatttttat taatgtacta aattactgtt ttgttaaatg caatttgct    2520 ttctcgggat tttaatatca aaatctattt agaaatacac aatattttgt tgcaggcttg    2580
ctggagaatc gatctgctat cataaaaatt acaaaaaaat tttatttgcc tcaattattt    2640
taggattggt attaaggacg cttaaattat ttgtcgggtc actacgcatc attgtgattg    2700
agaagatcag cgatacgaaa tattcgtagt actatcgata atttatttga aaattcataa    2760
gaaaagcaaa cgttacatga attgatgaaa caatacaaag acagataaag ccacgcacat    2820
ttaggatatt ggccgagatt actgaatatt gagtaagatc acggaatttc tgacaggagc    2880
atgtcttcaa ttcagcccaa atggcagttg aaatactcaa accgccccat atgcaggagc    2940
ggatcattca ttgtttgttt ggttgccttt gccaacatgg gagtccaagg tt    2992
```

SYNTHETIC BI-DIRECTIONAL PLANT PROMOTER

CROSS-REFERENCE TO RELATED APPLICATION

Figure 1:
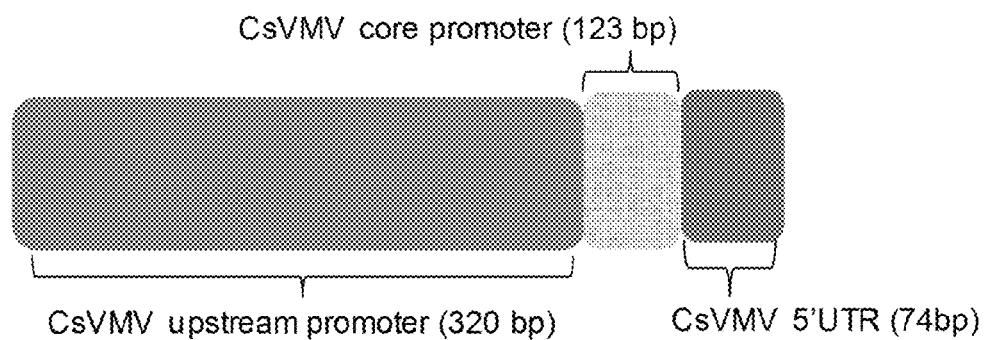

This application claims the benefit of the filing date of U.S. Provisional Patent Application Ser. No. 62/078,205, filed Nov. 11, 2014, for "SYNTHETIC BI DIRECTIONAL PLANT PROMOTER," the disclosure of which is hereby incorporated herein in its entirety by this reference.

TECHNICAL FIELD

The present disclosure generally relates to compositions and methods for promoting transcription of a nucleotide sequence in a plant or plant cell. Some embodiments relate to a synthetic Cassava Vein Mosaic Virus (CsVMV) bi-directional promoter that functions in plants to promote transcription of an operably linked nucleotide sequence. Particular embodiments relate to methods including a synthetic promoter (e.g., to introduce a nucleic acid molecule into a cell) and cells, cell cultures, tissues, organisms, and parts of organisms comprising a synthetic promoter, as well as products produced therefrom.

BACKGROUND

Many plant species are capable of being transformed with transgenes from other species to introduce agronomically desirable traits or characteristics, for example; improving nutritional value quality, increasing yield, conferring pest or disease resistance, increasing drought and stress tolerance, improving horticultural qualities (such as pigmentation and growth), imparting herbicide resistance, enabling the production of industrially useful compounds and/or materials from the plant, and/or enabling the production of pharmaceuticals. The introduction of transgenes into plant cells and the subsequent recovery of fertile transgenic plants that contain a stably integrated copy of the transgene can result in the production of transgenic plants that possess the desirable traits or characteristics.

Control and regulation of gene expression can occur through numerous mechanisms. Transcription initiation of a gene is a predominant controlling mechanism of gene expression. Initiation of transcription is generally controlled by polynucleotide sequences located in the 5'-flanking or upstream region of the transcribed gene. These sequences are collectively referred to as promoters. Promoters generally contain signals for RNA polymerase to begin transcription so that messenger RNA (mRNA) can be produced. Mature mRNA is transcribed by ribosomes, thereby synthesizing proteins. DNA-binding proteins interact specifically with promoter DNA sequences to promote the formation of a transcriptional complex and initiate the gene expression process. There are a variety of eukaryotic promoters isolated and characterized from plants that are functional for driving the expression of a transgene in plants. Promoters that affect gene expression in response to environmental stimuli, nutrient availability, or adverse conditions including heat shock, anaerobiosis, or the presence of heavy metals have been isolated and characterized. There are also promoters that control gene expression during development or in a tissue, or organ specific fashion. In addition, prokaryotic promoters isolated from bacteria and viruses have been isolated and characterized that are functional for driving the expression of a transgene in plants.

A typical promoter that is capable of expression in a eukaryote consists of a minimal promoter and other cis-elements. The minimal promoter is essentially a TATA box region where RNA polymerase II (polII), TATA-binding protein (TBP), and TBP-associated factors (TAFs) may bind to initiate transcription. However, in most instances, sequence elements other than the TATA motif are required for accurate transcription. Such sequence elements (e.g., enhancers) have been found to elevate the overall level of expression of the nearby genes, often in a position- and/or orientation-independent manner. Other sequences near the transcription start site (e.g., INR sequences) of some polII genes may provide an alternate binding site for factors that also contribute to transcriptional activation, even alternatively providing the core promoter binding sites for transcription in promoters that lack functional TATA elements. Zenzie-Gregory et al. (1992) *J. Biol. Chem.* 267: 2823-30.

Other gene regulatory elements include sequences that interact with specific DNA-binding factors. These sequence motifs are sometimes referred to as cis-elements, and are usually position- and orientation-dependent, though they may be found 5' or 3' to a gene's coding sequence, or in an intron. Such cis-elements, to which tissue-specific or development-specific transcription factors bind, individually or in combination, may determine the spatiotemporal expression pattern of a promoter at the transcriptional level. The arrangement of upstream cis-elements, followed by a minimal promoter, typically establishes the polarity of a particular promoter. Promoters in plants that have been cloned and widely used for both basic research and biotechnological application are generally unidirectional, directing only one gene that has been fused at its 3' end (i.e., downstream). See, Xie et al. (2001) *Nat. Biotechnol.* 19 (7): 677-9; U.S. Pat. No. 6,388,170.

Many cis-elements (or "upstream regulatory sequences") have been identified in plant promoters. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, e.g., Langridge et al. (1989) *Proc. Natl. Acad. Sci. USA* 86:3219-23. The type of control of specific promoter elements is typically an intrinsic quality of the promoter; i.e., a heterologous gene under the control of such a promoter is likely to be expressed according to the control of the native gene from which the promoter element was isolated. Id. These elements also typically may be exchanged with other elements and maintain their characteristic intrinsic control over gene expression.

It is often necessary to introduce multiple genes into plants for metabolic engineering and trait stacking, which genes are frequently controlled by identical or homologous promoters. However, homology-based gene silencing (HBGS) is likely to arise when multiple introduced transgenes have homologous promoters driving them. Mol et al. (1989) *Plant Mol. Biol.* 13:287-94. Thus, HBGS has been reported to occur extensively in transgenic plants. See, e.g., Vaucheret and Fagard (2001) *Trends Genet.* 17:29-35. Several mechanisms have been suggested to explain the phenomena of HBGS, all of which include the feature that sequence homology in the promoter triggers cellular recognition mechanisms that result in silencing of the repeated genes. Matzke and Matzke (1995 47:23-48; Fire (1999) *Trends Genet.* 15:358-63; Hamilton and Baulcombe (1999)

Science 286:950-2; Steimer et al. (2000) *Plant Cell* 12:1165-78. Furthermore, the repeated use of the same promoter to obtain similar levels of expression patterns of different transgenes can result in an excess of competing transcription factor (TF)-binding sites in repeated promoters can cause depletion of endogenous TFs and lead to transcriptional down-regulation.

Given that there is an ever greater need for integration of robustly expressing multigenic traits within a single locus of a transgenic event; solutions that provide for reducing the technical challenges associated with creating such transgenic events are of importance. More specifically, strategies to avoid HBGS in transgenic plants that involve the development of synthetic promoters that are functionally equivalent but have minimal sequence homology are desirable. When such synthetic promoters are used for expressing transgenes in crop plants, they may aid in avoiding or reducing HBGS. Mourrain et al. (2007) *Planta* 225(2):365-79; Bhullar et al. (2003) *Plant Physiol.* 132:988-98.

BRIEF SUMMARY

In embodiments of the subject disclosure, the disclosure relates to a synthetic Cassava Vein Mosaic Virus (CsVMV) bi-directional polynucleotide promoter comprising a plurality of promoter elements from an *Arabidopsis thaliana* Ubiquitin-10 promoter and a Cassava Vein Mosaic Virus promoter. In a further embodiment, the subject disclosure comprises various promoter elements. Accordingly, the promoter elements comprise an intron. In some instances the promoter elements comprise a 5'-UTR. In addition, the promoter elements comprise an upstream promoter element. Furthermore, the promoter elements comprise a minimal core promoter. In embodiments of the subject disclosure, the disclosure relates to a method for producing a transgenic plant cell, comprising the steps of: a) transforming a plant cell with a gene expression cassette comprising a synthetic CsVMV bi-directional polynucleotide promoter operably linked to at least one polynucleotide sequence of interest; b) isolating the transformed plant cell comprising the gene expression cassette; and, c) producing a transgenic plant cell comprising the synthetic CsVMV bi-directional polynucleotide promoter operably linked to at least one polynucleotide sequence of interest. In embodiments of the subject disclosure, the disclosure relates to a method for expressing a polynucleotide sequence of interest in a plant cell, the method comprising introducing into the plant cell the polynucleotide sequence of interest operably linked to a synthetic CsVMV bi-directional polynucleotide promoter. In embodiments of the subject disclosure, the disclosure relates to a transgenic plant cell comprising the synthetic CsVMV bi-directional polynucleotide promoter.

The foregoing and other features will become more apparent from the following detailed description of several embodiments, which proceeds with reference to the accompanying figures.

BRIEF DESCRIPTION OF THE FIGURES

FIG. 1: This figure is a schematic of the Cassava Vein Mosaic Virus promoter ("CsVMV") that is 517 bp in length. The minimal core promoter ("CsVMV core promoter") has been identified as a 123 bp region, and is located approximately 320 bp downstream of the 5' end of the promoter. Included in the schematic of the CsVMV promoter is the 5' UTR region ("CsVMV 5' UTR") which is 74 bp in length.

FIG. 2: This figure is a schematic of the *Arabidopsis thaliana* Ubiquitin 10 promoter ("AtUbi10") that is 1,332 bp in length. The minimal core promoter ("AtUbi10 core promoter") was identified as the 140 bp region, and is located 836 bp downstream of the 5' end of the promoter. Included in the schematic of the AtUbi10 promoter is the 5' UTR region ("AtUbi10 5'UTR") which is 74 bp in length, and the intron ("At Ubi10 Intron") which is 304 bp in length.

FIG. 3: This figure provides microscopy images of particle bombarded soybean immature embryos for expression of the GFP and RFP proteins. The transient expression of the gfp and rfp, transgenes pDAB113198 (198 GFP and 198 RFP), pDAB113199 (199 GFP and 199 RFP), pDAB113192 (192 GFP and 192 RFP), and pDAB113194 (194 GFP and 194 RFP) within the soybean plant cell resulted in expression levels of Green Fluorescent Protein and Red Fluorescent Protein at levels that were equivalent to the expression of the gfp and rfp, transgenes in the control constructs pDAB113188 (188 GFP and 188 RFP) and pDAB113190 (190 GFP and 190 RFP).

FIG. 4: This graph is the RFP/GFP foci count obtained from CsVMV and AtUbi10 bi-directional promoters compared to unidirectional polar promoters.

FIG. 5: This figure provides microscopy images of particle bombarded maize embryos for GFP and RFP expression. The transient expression of the gfp and rfp, transgenes pDAB113198, pDAB113199, pDAB113192, pDAB113194, pDAB113193, pDAB113196, and pDAB113197 within the maize plant cell resulted in expression of the Green Fluorescent Protein (Panel A) and Red Fluorescent Protein (Panel B).

FIG. 6: This graph illustrates the relative expression volume, correlating to fluorescent intensity for expression of the RFP and GFP proteins by the bi-directional promoters.

DETAILED DESCRIPTION

I. Overview of Several Embodiments

Development of transgenic plants is becoming increasingly complex, and typically requires stacking multiple transgenes into a single locus. See Xie et al. (2001) *Nat. Biotechnol.* 19 (7):677-9. Since each transgene usually requires a unique promoter for expression, multiple promoters are required to express different transgenes within one gene stack. In addition to increasing the size of the gene stack, this frequently leads to repeated use of the same promoter to obtain similar levels of expression patterns of different transgenes. This approach is often problematic, as the expression of multiple transgenes driven by the same promoter may lead to gene silencing or HBGS. An excess of competing transcription factor (TF)-binding sites in repeated promoters can cause depletion of endogenous TFs and lead to transcriptional down-regulation. The silencing of transgenes is undesirable to the performance of a transgenic plant produced to express the transgenes. Repetitive sequences within a transgene often lead to intra-locus homologous recombination resulting in polynucleotide rearrangements and undesirable phenotypes or agronomic performance.

Plant promoters used for basic research or biotechnological application are generally unidirectional, and regulate only one gene that has been fused at its 3' end (downstream). To produce transgenic plants with various desired traits or characteristics, it would be useful to reduce the number of promoters that are deployed to drive expression of the transgenes that encode the desired traits and characteristics. Especially in applications where it is necessary to introduce multiple transgenes into plants for metabolic engineering and trait stacking, thereby necessitating multiple promoters to drive the expression of multiple transgenes. By developing a single synthetic CsVMV bi-directional promoter that can drive expression of two transgenes that flank the promoter, the total numbers of promoters needed for the development of transgenic crops may be reduced, thereby lessening the repeated use of the same promoter, reducing the size of transgenic constructs, and/or reducing the possibility of HBGS. Such a promoter can be generated by introducing known cis-elements in a novel or synthetic stretch of DNA, or alternatively by "domain swapping," wherein domains of one promoter are replaced with functionally equivalent domains from other heterologous promoters.

Embodiments herein utilize a process wherein a unidirectional promoter from a *Arabidopsis thaliana* ubiquitin-10 gene (e.g., AtUbi10) and a Cassava Vein Mosaic Virus promoter (e.g., CsVMV) to design a synthetic CsVMV bi-directional promoter, such that one promoter can direct the expression of two genes, one on each end of the promoter. Synthetic CsVMV bi-directional promoters may allow those in the art to stack transgenes in plant cells and plants while lessening the repeated use of the same promoter and reducing the size of transgenic constructs. Furthermore, regulating the expression of two genes with a single synthetic CsVMV bi-directional promoter may also provide the ability to co-express the two genes under the same conditions, such as may be useful, for example, when the two genes each contribute to a single trait in the host. The use of bi-directional function of promoters in plants has been reported in some cases, including the *Zea mays* Ubiquitin 1 promoter (International Patent Publication No. WO2013101343 A1), CaMV 35 promoters (Barfield and Pua (1991) *Plant Cell Rep.* 10 (6-7):308-14; Xie et al. (2001), supra), and the mas promoters (Velten et al. (1984) *EMBO J.* 3(12):2723-30; Langridge et al. (1989) *Proc. Natl. Acad. Sci. USA* 86:3219-23).

Transcription initiation and modulation of gene expression in plant genes is directed by a variety of DNA sequence elements that are collectively arranged within the promoter. Eukaryotic promoters consist of minimal core promoter element (minP), and further upstream regulatory sequences (URSs). The core promoter element is a minimal stretch of contiguous DNA sequence that is sufficient to direct accurate initiation of transcription. Core promoters in plants also comprise canonical regions associated with the initiation of transcription, such as CAAT and TATA boxes. The TATA box element is usually located approximately 20 to 35 nucleotides upstream of the initiation site of transcription.

The activation of the minP is dependent upon the URS, to which various proteins bind and subsequently interact with the transcription initiation complex. URSs comprise of DNA sequences, which determine the spatiotemporal expression pattern of a promoter comprising the URS. The polarity of a promoter is often determined by the orientation of the minP, while the URS is bipolar (i.e., it functions independent of its orientation).

In specific examples of some embodiments, a minimal core promoter element (minUbi10P) of an *Arabidopsis thaliana* Ubi10 promoter (AtUbi10) originally derived from *Arabidopsis thaliana*, is used to engineer a synthetic CsVMV bi-directional promoter that functions in plants to provide expression control characteristics that are unique with respect to previously described bi-directional promoters. Embodiments include a synthetic CsVMV bi-directional promoter that further includes a minimal core promoter element nucleotide sequence derived from a native CsVMV promoter (minCsVMVP). In other embodiments, a minimal core promoter element of a modified Cassava vein mosaic virus promoter (CsVMV) originally derived from the Cassava vein mosaic virus, is used to engineer a synthetic bi-directional *Arabidopsis thaliana* Ubi10 promoter that may function in plants to provide expression control characteristics that are unique with respect to previously available bi-directional promoters. Embodiments include a synthetic bi-directional AtUbi10 promoter that further includes a minimal core promoter element nucleotide sequence derived from a native AtUbi10 promoter.

The AtUbi10 promoter comprises sequences that originate from the *Arabidopsis thaliana* genome. A modified AtUbi10 promoter that is used in some examples is an approximately 1.3 kb promoter that contains a TATA box; a 5'UTR; and an intron. Other *Arabidopsis thaliana* Ubiquitin promoter variants derived from *Arabidopsis* species and *Arabidopsis thaliana* genotypes may exhibit high sequence conservation around the minP element consisting of the TATA element. Thus, embodiments of the invention are exemplified by the use of this short, highly-conserved region (e.g., SEQ ID NO:1) of a AtUbi10 promoter as a minimal core promoter element for constructing synthetic bi-directional plant promoters.

The CsVMV promoter comprises sequences that originate from the Cassava Vein Mosaic Virus genome. A modified CsVMV promoter that is used in some examples is an approximately 0.5 kb promoter that contains a TATA box; and a 5'UTR. Other Cassava Vein Mosaic Virus promoter variants derived from Cassava virus species and Cassava Vein Mosaic Virus variants may exhibit high sequence conservation around the minP element consisting of the TATA element. Thus, embodiments of the invention are exemplified by the use of this short, highly-conserved region (e.g., SEQ ID NO:5) of a CsVMV promoter as a minimal core promoter element for constructing synthetic CsVMV bi-directional plant promoters.

II. Abbreviations

AtUbi10 *Arabidopsis thaliana* Ubiquitin 10
BCA bicinchoninic acid
CaMV cauliflower mosaic virus
CsVMV cassava vein mosaic virus
CTP chloroplast transit peptide
HBGS homology-based gene silencing
minUbi1P minimal core promoter
OLA oligo ligation amplification
PCR polymerase chain reaction
RCA rolling circle amplification
RT-PCR reverse transcriptase PCR
SNuPE single nucleotide primer extension
URS upstream regulatory sequence III. Terms Throughout the application, a number of terms are used. In order to provide a clear and consistent understanding of the specification and claims, including the scope to be given such terms, the following definitions are provided.

Introns: As used herein, the term "intron" refers to any nucleic acid sequence comprised in a gene (or expressed polynucleotide sequence of interest) that is transcribed but not translated. Introns include untranslated nucleic acid sequence within an expressed sequence of DNA, as well as the corresponding sequence in RNA molecules transcribed therefrom.

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Gene expression: The process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

Homology-based gene silencing: As used herein, "homology-based gene silencing" (HBGS) is a generic term that includes both transcriptional gene silencing and post-transcriptional gene silencing. Silencing of a target locus by an unlinked silencing locus can result from transcription inhibition (transcriptional gene silencing; TGS) or mRNA degradation (post-transcriptional gene silencing; PTGS), owing to the production of double-stranded RNA (dsRNA) corresponding to promoter or transcribed sequences, respectively. The involvement of distinct cellular components in each process suggests that dsRNA-induced TGS and PTGS likely result from the diversification of an ancient common mechanism. However, a strict comparison of TGS and PTGS has been difficult to achieve because it generally relies on the analysis of distinct silencing loci. We describe a single transgene locus that triggers both TGS and PTGS, owing to the production of dsRNA corresponding to promoter and transcribed sequences of different target genes. Mourrain et al. (2007) *Planta* 225:365-79. It is likely that siRNAs are the actual molecules that trigger TGS and PTGS on homologous sequences: the siRNAs would in this model trigger silencing and methylation of homologous sequences in cis and in trans through the spreading of methylation of transgene sequences into the endogenous promoter. Id.

Nucleic acid molecule: As used herein, the term "nucleic acid molecule" (or "nucleic acid" or "polynucleotide") may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide". A nucleic acid molecule is usually at least 10 bases in length, unless otherwise specified. The term may refer to a molecule of RNA or DNA of indeterminate length. The term includes single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by the sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" or "5'" relative to a further element if they are bonded or would be bonded to the same nucleic acid in the 5' direction from that element. Similarly, discrete elements may be "downstream" or "3'" relative to a further element if they are or would be bonded to the same nucleic acid in the 3' direction from that element.

A base "position," as used herein, refers to the location of a given base or nucleotide residue within a designated nucleic acid. The designated nucleic acid may be defined by alignment (see below) with a reference nucleic acid.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the Na+ and/or Mg2+ concentration) of the hybridization buffer will contribute to the stringency of hybridization, though wash times also influence stringency. Calculations regarding hybridization conditions required for attaining particular degrees of stringency are discussed in Sambrook et al. (ed.), *Molecular Cloning: A Laboratory Manual*, 2nd ed., vol. 1-3, Cold Spring Harbor Laboratory Press, Cold Spring Harbor, N.Y., 1989, chs. 9 and 11.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes.

The following are representative, non-limiting hybridization conditions:

Very High Stringency: Hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2×-3×SSC buffer at room temperature to 55° C. for 20-30 minutes each.

In particular embodiments, specifically hybridizable nucleic acid molecules can remain bound under very high stringency hybridization conditions. In these and further embodiments, specifically hybridizable nucleic acid molecules can remain bound under high stringency hybridization conditions. In these and further embodiments, specifically hybridizable nucleic acid molecules can remain bound under moderate stringency hybridization conditions.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer", which allows a DNA polymerase to extend the oligonucleotide and replicate the complementary strand.

Sequence identity: The term "sequence identity" or "identity", as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50. A detailed consideration of sequence alignment methods and homology calculations can be found in, e.g., Altschul et al. (1990) *J. Mol. Biol.* 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

Operably linked: A first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked Promoter: A region of DNA that generally is located upstream (towards the 5' region of a gene) that is needed for transcription. Promoters may permit the proper activation or repression of the gene which they control. A promoter may contain specific sequences that are recognized by transcription factors. These factors may bind to the promoter DNA sequences and result in the recruitment of RNA polymerase, an enzyme that synthesizes RNA from the coding region of the gene.

Transformed: A cell is "transformed" by a nucleic acid molecule transduced into the cell when the nucleic acid molecule becomes stably replicated by the cell, either by incorporation of the nucleic acid molecule into the cellular genome or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319:791-3); lipofection (Felgner et al. (1987) Proc. Natl. Acad. Sci. USA 84:7413-7); microinjection (Mueller et al. (1978) Cell 15:579-85); Agrobacterium-mediated transfer (Fraley et al. (1983) Proc. Natl. Acad. Sci. USA 80:4803-7); direct DNA uptake; whiskers-mediated transformation; and microprojectile bombardment (Klein et al. (1987) Nature 327:70).

Transgene: An exogenous nucleic acid sequence. In one example, a transgene is a gene sequence (e.g., an herbicide-resistance gene), a gene encoding an industrially or pharmaceutically useful compound, or a gene encoding a desirable agricultural trait. In yet another example, the transgene is an antisense nucleic acid sequence, wherein expression of the antisense nucleic acid sequence inhibits expression of a target nucleic acid sequence. A transgene may contain regulatory sequences operably linked to the transgene (e.g., a promoter). In some embodiments, a polynucleotide sequence of interest is a transgene. However, in other embodiments, a polynucleotide sequence of interest is an endogenous nucleic acid sequence, wherein additional genomic copies of the endogenous nucleic acid sequence are desired, or a nucleic acid sequence that is in the antisense orientation with respect to the sequence of a target nucleic acid molecule in the host organism.

Transgenic Event: A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

Vector: A nucleic acid molecule as introduced into a cell, thereby producing a transformed cell. A vector may include nucleic acid sequences that permit it to replicate in the host cell, such as an origin of replication. Examples include, but are not limited to, a plasmid, cosmid, bacteriophage, or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector. A vector may optionally include materials to aid in achieving entry of the nucleic acid molecule into the cell (e.g., a liposome, protein coding, etc.).

Unless otherwise specifically explained, all technical and scientific terms used herein have the same meaning as commonly understood by those of ordinary skill in the art to which this disclosure belongs. Definitions of common terms in molecular biology can be found in, for example: Lewin, Genes V, Oxford University Press, 1994 (ISBN 0-19-854287-9); Kendrew et al. (eds.), The Encyclopedia of Molecular Biology, Blackwell Science Ltd., 1994 (ISBN 0-632-02182-9); and Meyers (ed.), Molecular Biology and Biotechnology: A Comprehensive Desk Reference, VCH Publishers, Inc., 1995 (ISBN 1-56081-569-8).

As used herein, the articles, "a," "an," and "the" include plural references unless the context clearly and unambiguously dictates otherwise.

IV. Synthetic Bi-Directional Promoter, CsVMV or AtUbi10, and Nucleic Acids Comprising the Same This disclosure provides nucleic acid molecules comprising a synthetic nucleotide sequence that may function as a bi-directional promoter. In some embodiments, a synthetic CsVMV bi-directional promoter may be operably linked to one or two polynucleotide sequence(s) of interest. For example, the synthetic CsVMV bi-directional promoter may be operably linked to one or two polynucleotide sequence(s) of interest that encode a gene (e.g., two genes, one on each end of the promoter), so as to regulate transcription of at least one (e.g., one or both) of the nucleotide sequence(s) of interest. In some embodiments, by incorporating a URS from a CsVMV promoter in the synthetic CsVMV bi-directional promoter, particular expression and regulatory patterns (e.g., such as are exhibited by genes under the control of the CsVMV promoter) may be achieved with regard to a polynucleotide sequence of interest that is operably linked to the synthetic CsVMV bi-directional promoter. In other embodiments, by incorporating a URS from an AtUbi10 promoter in the synthetic CsVMV bi-directional promoter, particular expression and regulatory patterns (e.g., such as are exhibited by genes under the control of the AtUbi10 promoter) may be achieved with regard to a polynucleotide sequence of interest that is operably linked to the synthetic CsVMV bi-directional promoter.

Some embodiments of the invention are exemplified herein by incorporating a minimal core promoter element from a unidirectional Arabidopsis thaliana ubiquitin-10 gene (AtUbi10) promoter into a molecular context different from that of the native promoter to engineer a synthetic CsVMV bi-directional promoter. This minimal core promoter element is referred to herein as "minUbi10P," and is approximately 140 bp in length. Sequencing and analysis of minUbi10P elements may preserve the function as an initiator of transcription if it shares, for example, at least about 75%; at least about 80%; at least about 85%; at least about 90%; at least about 91%; at least about 92%; at least about 93%; at least about 94%; at least about 95%; at least about 96%; at least about 97%; at least about 98%; at least about 99%; and/or at least about 100% sequence identity to the minUbi10P element of SEQ ID NO:1. Characteristics of minUbi10P elements that may be useful in some embodiments of the invention may include, for example and without limitation, the aforementioned high conservation of nucleotide sequence; the presence of at least one TATA box. In particular minUbi10P elements may be overlapping within the minUbi10P sequence.

In embodiments, the process of incorporating a minUbi10P element into a molecular context different from that of a native promoter to engineer a synthetic CsVMV bi-directional promoter may comprise incorporating the minUbi10P element into a CsVMV promoter nucleic acid or a AtUbi10 promoter nucleic acid, while reversing the orientation of the minUbi10P element with respect to the native sequence of the CsVMV or AtUbi10 promoter. Thus, a synthetic CsVMV or AtUbi10 bi-directional promoter may comprise a minUbi10P minimal core promoter element located 5' of, and in reverse orientation with respect to, a CsVMV or AtUbi10 promoter nucleotide sequence, such that it may be operably linked to a polynucleotide sequence of interest located 5' of the CsVMV or AtUbi10 promoter nucleotide sequence. For example, the minUbi10P element may be incorporated at the 5' end of a CsVMV or AtUbi10 promoter in reverse orientation.

Some embodiments of the invention are exemplified herein by incorporating a minimal core promoter element from a unidirectional Cassava Vein Mosaic Virus gene (CsVMV) promoter into a molecular context different from that of the native promoter to engineer a synthetic CsVMV bi-directional promoter. This minimal core promoter element is referred to herein as "minCsVMVP," and is approximately 123 bp in length. Sequencing and analysis of minCsVMVP elements may preserve its function as an initiator of transcription if it shares, for example, at least about 75%; at least about 80%; at least about 85%; at least about 90%; at least about 91%; at least about 92%; at least about 93%; at least about 94%; at least about 95%; at least about 96%; at least about 97%; at least about 98%; at least about 99%; and/or at least about 100% sequence identity to the minCsVMVP element of SEQ ID NO:5. Characteristics of minCsVMVP elements that may be useful in some embodiments of the invention may include, for example and without limitation, the aforementioned high conservation of nucleotide sequence; the presence of at least one TATA box. In particular minCsVMVP elements may be overlapping within the minCsVMVP sequence.

In embodiments, the process of incorporating a minCsVMVP element into a molecular context different from that of a native promoter to engineer a synthetic CsVMV bi-directional promoter may comprise incorporating the minCsVMVP element into a CsVMV promoter nucleic acid or a AtUbi10 promoter nucleic acid, while reversing the orientation of the minCsVMVP element with respect to the remaining sequence of the CsVMV or AtUbi10 promoter. Thus, a synthetic CsVMV or AtUbi10 bi-directional promoter may comprise a minCsVMVP minimal core promoter element located 5' of, and in reverse orientation with respect to, a CsVMV or AtUbi10 promoter nucleotide sequence, such that it may be operably linked to a polynucleotide sequence of interest located 5' of the CsVMV or AtUbi10 promoter nucleotide sequence. For example, the minCsVMVP element may be incorporated at the 5' end of a CsVMV or AtUbi10 promoter in reverse orientation.

A synthetic CsVMV bi-directional promoter may also comprise one or more additional sequence elements in addition to a minUbi10P element and elements of a native CsVMV promoter including the minCsVMVP. In some embodiments, a synthetic CsVMV bi-directional promoter may comprise a promoter URS; an exon (e.g., a leader or signal peptide); an intron; a spacer sequence; and or combinations of one or more of any of the foregoing. For example and without limitation, a synthetic CsVMV bi-directional promoter may comprise a URS sequence from a CsVMV promoter; an intron from a ADH gene; an exon encoding a leader peptide from an AtUbi10 gene; an intron from an AtUbi10 gene; and combinations of these.

A synthetic bi-directional AtUbi10 promoter may also comprise one or more additional sequence elements in addition to a minCsVMVP element and elements of a native AtUbi10 promoter including the minUbi10P. In some embodiments, a synthetic bi-directional AtUbi10 promoter may comprise a promoter URS; an exon (e.g., a leader or signal peptide); an intron; a spacer sequence; and or combinations of one or more of any of the foregoing. For example and without limitation, a synthetic bi-directional AtUbi10 promoter may comprise a URS sequence from a AtUbi10 promoter; an intron from a ADH gene; an exon encoding a leader peptide from an AtUbi10 gene; an intron from an AtUbi10 gene; and combinations of these.

In some embodiments of a promoter comprising a promoter URS, the URS may be selected to confer particular regulatory properties on the synthetic promoter. Known promoters vary widely in the type of control they exert on operably linked genes (e.g., environmental responses, developmental cues, and spatial information), and a URS incorporated into a heterologous promoter typically maintains the type of control the URS exhibits with regard to its native promoter and operably linked gene(s). Langridge et al. (1989), supra. Examples of eukaryotic promoters that have been characterized and may contain a URS comprised within a synthetic bi-directional *Zea mays* Ubiquitin 1 promoter according to some embodiments include, for example and without limitation: those promoters described in U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. No. 6,433,252 (maize L3 oleosin promoter); U.S. Pat. No. 6,429,357 (rice actin 2 promoter, and rice actin 2 intron); U.S. Pat. No. 5,837,848 (root-specific promoter); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bi-directional promoters); U.S. Pat. No. 6,635,806 (gamma-coixin promoter); and U.S. patent application Ser. No. 09/757,089 (maize chloroplast aldolase promoter).

Additional exemplary prokaryotic promoters include the nopaline synthase (NOS) promoter (Ebert et al. (1987) *Proc. Natl. Acad. Sci. USA* 84 (16):5745-9); the octopine synthase (OCS) promoter (which is carried on tumor-inducing plasmids of *Agrobacterium tumefaciens*); the caulimovirus promoters such as the cauliflower mosaic virus (CaMV) 19S promoter (Lawton et al. (1987) *Plant Mol. Biol.* 9:315-24); the CaMV 35S promoter (Odell et al. (1985) *Nature* 313: 810-2; the figwort mosaic virus 35S-promoter (Walker et al. (1987) *Proc. Natl. Acad. Sci. USA* 84 (19):6624-8); the sucrose synthase promoter (Yang and Russell (1990) *Proc. Natl. Acad. Sci. USA* 87:4144-8); the R gene complex promoter (Chandler et al. (1989) *Plant Cell* 1:1175-83); CaMV35S (U.S. Pat. Nos. 5,322,938, 5,352,605, 5,359,142, and 5,530,196); FMV 35S (U.S. Pat. Nos. 6,051,753, and 5,378,619); a PC1SV promoter (U.S. Pat. No. 5,850,019);

the SCP1 promoter (U.S. Pat. No. 6,677,503); and *Agrobacterium tumefaciens* Nos promoters (GenBank Accession No. V00087; Depicker et al. (1982) *J. Mol. Appl. Genet.* 1:561-73; Bevan et al. (1983) *Nature* 304:184-7), and the like.

In some embodiments, a synthetic CsVMV bi-directional promoter may further comprise an exon. For example, it may be desirable to target or traffic a polypeptide encoded by a polynucleotide sequence of interest operably linked to the promoter to a particular subcellular location and/or compartment. In these and other embodiments, a coding sequence (exon) may be incorporated into a nucleic acid molecule between the remaining synthetic CsVMV bi-directional promoter sequence and a nucleotide sequence encoding a polypeptide. These elements may be arranged according to the discretion of the skilled practitioner such that the synthetic CsVMV bi-directional promoter promotes the expression of a polypeptide (or one or both of two polypeptide-encoding sequences that are operably linked to the promoter) comprising the peptide encoded by the incorporated coding sequence in a functional relationship with the remainder of the polypeptide. In particular examples, an exon encoding a leader, transit, or signal peptide (e.g., an *Arabidopsis thaliana* Ubi10 leader peptide) may be incorporated.

Peptides that may be encoded by an exon incorporated into a synthetic CsVMV bi-directional promoter include, for example and without limitation: a Ubiquitin (e.g., *Arabidopsis thaliana* Ubi10) leader peptide; a chloroplast transit peptide (CTP) (e.g., the *A. thaliana* EPSPS CTP (Klee et al. (1987) *Mol. Gen. Genet.* 210:437-42), and the *Petunia hybrida* EPSPS CTP (della-Cioppa et al. (1986) *Proc. Natl. Acad. Sci. USA* 83:6873-7)), as exemplified for the chloroplast targeting of dicamba monooxygenase (DMO) in International PCT Publication No. WO 2008/105890.

Introns may also be incorporated in a synthetic CsVMV bi-directional promoter in some embodiments of the invention, for example, between the remaining synthetic CsVMV bi-directional promoter sequence and a polynucleotide sequence of interest that is operably linked to the promoter. In some examples, an intron incorporated into a synthetic CsVMV bi-directional promoter may be, without limitation, a 5' UTR that functions as a translation leader sequence that is present in a fully processed mRNA upstream of the translation start sequence (such a translation leader sequence may affect processing of a primary transcript to mRNA, mRNA stability, and/or translation efficiency). Examples of translation leader sequences include maize and petunia heat shock protein leaders (U.S. Pat. No. 5,362,865), plant virus coat protein leaders, plant rubisco leaders, and others. See, e.g., Turner and Foster (1995) *Molecular Biotech.* 3(3):225-36. Non-limiting examples of 5' UTRs include GmHsp (U.S. Pat. No. 5,659,122); PhDnaK (U.S. Pat. No. 5,362,865); AtAntl; TEV (Carrington and Freed (1990) *J. Virol.* 64:1590-7); and AGRtunos (GenBank Accession No. V00087; and Bevan et al. (1983) *Nature* 304:184-7). In particular examples, an *Arabidopsis thaliana* Ubiquitin 10 intron may be incorporated in a synthetic CsVMV bi-directional promoter.

Additional sequences that may optionally be incorporated into a synthetic CsVMV bi-directional promoter include, for example and without limitation: 3' non-translated sequences; 3' transcription termination regions; and polyadenylation regions. These are genetic elements located downstream of a polynucleotide sequence of interest (e.g., a gene sequence of interest that is operably linked to a synthetic CsVMV bi-directional promoter), and include polynucleotides that provide polyadenylation signal, and/or other regulatory signals capable of affecting transcription, mRNA processing, or gene expression. A polyadenylation signal may function in plants to cause the addition of polyadenylate nucleotides to the 3' end of a mRNA precursor. The polyadenylation sequence may be derived from the natural gene, from a variety of plant genes, or from T-DNA genes. A non-limiting example of a 3' transcription termination region is the nopaline synthase 3' region (nos 3; Fraley et al. (1983) *Proc. Natl. Acad. Sci. USA* 80:4803-7). An example of the use of different 3' nontranslated regions is provided in Ingelbrecht et al. (1989), *Plant Cell* 1:671-80. Non-limiting examples of polyadenylation signals include one from a *Pisum sativum* RbcS2 gene (Ps.RbcS2-E9; Coruzzi et al. (1984) *EMBO J.* 3:1671-9) and *Agrobacterium tumefaciens* Nos gene (GenBank Accession No. E01312).

In some embodiments, a synthetic CsVMV bi-directional promoter comprises one or more nucleotide sequence(s) that facilitate targeting of a nucleic acid comprising the promoter to a particular locus in the genome of a target organism. For example, one or more sequences may be included that are homologous to segments of genomic DNA sequence in the host (e.g., rare or unique genomic DNA sequences). In some examples, these homologous sequences may guide recombination and integration of a nucleic acid comprising a synthetic CsVMV bi-directional promoter at the site of the homologous DNA in the host genome. In particular examples, a synthetic CsVMV bi-directional promoter comprises one or more nucleotide sequences that facilitate targeting of a nucleic acid comprising the promoter to a rare or unique location in a host genome utilizing engineered nuclease enzymes that recognize sequence at the rare or unique location and facilitate integration at that rare or unique location. Such a targeted integration system employing zinc-finger endonucleases as the nuclease enzyme is described in U.S. patent application Ser. No. 13/011,735, the contents of the entirety of which are incorporated herein by this reference.

In other embodiments, the disclosure further includes as an embodiment the polynucleotide sequence of interest comprising a trait. The trait can be an insecticidal resistance trait, herbicide tolerance trait, nitrogen use efficiency trait, water use efficiency trait, nutritional quality trait, DNA binding trait, selectable marker trait, and any combination thereof.

In further embodiments the traits are integrated within the transgenic plant cell as a transgenic event. In additional embodiments, the transgenic event produces a commodity product. Accordingly, a composition is derived from transgenic plant cells of the subject disclosure, wherein said composition is a commodity product selected from the group consisting of meal, flour, protein concentrate, or oil. In further embodiments, commodity products produced by transgenic plants derived from transformed plant cells are included, wherein the commodity products comprise a detectable amount of a nucleic acid sequence of the invention. In some embodiments, such commodity products may be produced, for example, by obtaining transgenic plants and preparing food or feed from them. Commodity products comprising one or more of the nucleic acid sequences of the invention includes, for example and without limitation: meals, oils, crushed or whole grains or seeds of a plant, and any food product comprising any meal, oil, or crushed or whole grain of a recombinant plant or seed comprising one or more of the nucleic acid sequences of the invention. The detection of one or more of the sequences of the invention in one or more commodity or commodity products is de facto evidence that the commodity or commodity product is produced from a transgenic plant designed to express one or more agronomic traits.

Nucleic acids comprising a synthetic CsVMV bi-directional promoter may be produced using any technique known in the art, including for example and without limitation: RCA; PCR amplification; RT-PCR amplification; OLA; and SNuPE. These and other equivalent techniques are well known to those of skill in the art, and are further described in detail in, for example and without limitation: Sambrook et al. *Molecular Cloning: A Laboratory Manual,* 3rd Ed., Cold Spring Harbor Laboratory, 2001; and Ausubel et al. *Current Protocols in Molecular Biology*, John Wiley & Sons, 1998. All of the references cited above, including both of the foregoing manuals, are incorporated herein by this reference in their entirety, including any drawings, figures, and/or tables provided therein.

V. Delivery to a Cell of a Nucleic Acid Molecule Comprising Synthetic Bi-Directional Promoter, CsVMV The present disclosure also provides methods for transforming a cell with a nucleic acid molecule comprising a synthetic CsVMV bi-directional promoter. Any of the large number of techniques known in the art for introduction of nucleic acid molecules into plants may be used to transform a plant with a nucleic acid molecule comprising a synthetic CsVMV bi-directional promoter according to some embodiments, for example, to introduce one or more synthetic CsVMV bi-directional promoters into the host plant genome, and/or to further introduce one or more nucleotides of interest operably linked to the promoter.

Suitable methods for transformation of plants include any method by which DNA can be introduced into a cell, for example and without limitation: electroporation (see, e.g., U.S. Pat. No. 5,384,253); microprojectile bombardment (see, e.g., U.S. Pat. Nos. 5,015,580, 5,550,318, 5,538,880, 6,160,208, 6,399,861, and 6,403,865); *Agrobacterium*-mediated transformation (see, e.g., U.S. Pat. Nos. 5,635,055, 5,824,877, 5,591,616; 5,981,840, and 6,384,301); and protoplast transformation (see, e.g., U.S. Pat. No. 5,508,184). Through the application of techniques such as the foregoing, the cells of virtually any plant species may be stably transformed, and these cells may be developed into transgenic plants by techniques known to those of skill in the art. For example, techniques that may be particularly useful in the context of cotton transformation are described in U.S. Pat. Nos. 5,846,797, 5,159,135, 5,004,863, and 6,624,344; techniques for transforming *Brassica* plants in particular are described, for example, in U.S. Pat. No. 5,750,871; techniques for transforming soya are described, for example, in U.S. Pat. No. 6,384,301; and techniques for transforming maize are described, for example, in U.S. Pat. Nos. 7,060,876 and 5,591,616, and International PCT Publication WO 95/06722.

After effecting delivery of an exogenous nucleic acid to a recipient cell, the transformed cell is generally identified for further culturing and plant regeneration. In order to improve the ability to identify transformants, one may desire to employ a selectable or screenable marker gene with the transformation vector used to generate the transformant. In this case, the potentially transformed cell population can be assayed by exposing the cells to a selective agent or agents, or the cells can be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of the desired nucleic acid molecule comprising a synthetic CsVMV bi-directional promoter in the regenerating plants, a variety of assays may be performed. Such assays include, for example: molecular biological assays, such as Southern and Northern blotting and PCR; biochemical assays, such as detecting the presence of a protein product, e.g., by immunological means (ELISA and/or Western blots), or by enzymatic function; plant part assays, such as leaf or root assays; and analysis of the phenotype of the whole regenerated plant.

Targeted integration events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (see, e.g., Rios et al. (2002) *Plant J.* 32:243-53), and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two may be produced. Thus, PCR genotyping strategies may include, for example and without limitation: amplification of specific sequences in the plant genome; amplification of multiple specific sequences in the plant genome; amplification of non-specific sequences in the plant genome; and combinations of any of the foregoing. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule, for example, at a sequence corresponding to a coding region within a polynucleotide sequence of interest comprised therein, or other parts of the nucleic acid molecule. These primers may be used in conjunction with the primers described above. Oligonucleotide primers may be synthesized according to a desired sequence, and are commercially available (e.g., from Integrated DNA Technologies, Inc., Coralville, Iowa). Amplification may be followed by cloning and sequencing, or by direct sequence analysis of amplification products. One skilled in the art might envision alternative methods for analysis of amplification products

VI. Cells, Cell Cultures, Tissues, and Organisms Comprising Synthetic Bi-Directional Promoter, CsVMV Some embodiments of the present invention also provide cells comprising a synthetic CsVMV bi-directional promoter, for example, as may be present in a nucleic acid construct. In particular examples, a synthetic CsVMV bi-directional promoter according to some embodiments may be utilized as a regulatory sequence to regulate the expression of transgenes in plant cells and plants. In some such examples, the use of a synthetic CsVMV bi-directional promoter operably linked to a polynucleotide sequence of interest (e.g., a transgene) may reduce the number of homologous promoters needed to regulate expression of a given number of nucleotide sequences of interest, and/or reduce the size of the nucleic acid construct(s) required to introduce a given number of nucleotide sequences of interest. Furthermore, use of a synthetic CsVMV bi-directional promoter may allow co-expression of two operably linked polynucleotide sequence of interest under the same conditions (i.e., the conditions under which the CsVMV promoter is active). Such examples may be particularly useful, e.g., when the two operably linked nucleotide sequences of interest each contribute to a single trait in a transgenic host comprising the nucleotide sequences of interest, and co-expression of the nucleotide sequences of interest advantageously impacts expression of the trait in the transgenic host.

In some embodiments, a transgenic plant comprising one or more synthetic CsVMV bi-directional promoter(s) and/or nucleotide sequence(s) of interest may have one or more desirable traits conferred (e.g., introduced, enhanced, or contributed to) by expression of the nucleotide sequence(s) of interest in the plant. Such traits may include, for example and without limitation: resistance to insects, other pests, and disease-causing agents; tolerance to herbicides; enhanced stability, yield, or shelf-life; environmental tolerances; pharmaceutical production; industrial product production; and nutritional enhancements. In some examples, a desirable trait may be conferred by transformation of a plant with a nucleic acid molecule comprising a synthetic CsVMV bi-directional promoter operably linked to a polynucleotide sequence of interest. In some examples, a desirable trait may be conferred to a plant produced as a progeny plant via breeding, which trait may be conferred by one or more nucleotide sequences of interest operably linked to a synthetic CsVMV bi-directional promoter that is/are passed to the plant from a parent plant comprising a polynucleotide sequence of interest operably linked to a synthetic CsVMV bi-directional promoter.

A transgenic plant according to some embodiments may be any plant capable of being transformed with a nucleic acid molecule of the invention, or of being bred with a plant transformed with a nucleic acid molecule of the invention. Accordingly, the plant may be a dicot or monocot. Non-limiting examples of dicotyledonous plants for use in some examples include: alfalfa; beans; broccoli; cabbage; canola; carrot; cauliflower; celery; Chinese cabbage; cotton; cucumber; eggplant; lettuce; melon; pea; pepper; peanut; potato; pumpkin; radish; rapeseed; spinach; soybean; squash; sugarbeet; sunflower; tobacco; tomato; and watermelon. Non-limiting examples of monocotyledonous plants for use in some examples include: *Brachypodium*; corn; onion; rice; sorghum; wheat; rye; millet; sugarcane; oat; triticale; switchgrass; and turfgrass.

In some embodiments, a transgenic plant may be used or cultivated in any manner, wherein presence a synthetic CsVMV bi-directional promoter and/or operably linked polynucleotide sequence of interest is desirable. Accordingly, such transgenic plants may be engineered to, inter alia, have one or more desired traits or transgenic events, by being transformed with nucleic acid molecules according to the invention, and may be cropped or cultivated by any method known to those of skill in the art The following examples are provided to illustrate certain particular features and/or embodiments. The examples should not be construed to limit the disclosure to the particular features or embodiments exemplified.

EXAMPLES

Example 1: Annotation of the Cassava Vein Mosaic Virus (CsVMV) Promoter Elements The CsVMV promoter (SEQ ID NO:9; FIG. 1) is a 517 bp polynucleotide sequence (U.S. Pat. No. 7,053,205). The polynucleotide sequence can be divided into three portions. The first portion is a 320 bp, 5' upstream promoter polynucleotide fragment. The second portion is proximally located downstream of the 5' upstream promoter portion (URS). The second portion contains a 123 bp core promoter (minCsVMVP). The two portions are further attached to a third portion. The third portion is a 74 bp, 5' UnTranslated Region (UTR) which is further located downstream of the 5' upstream promoter and the 123 bp core promoter.

The polynucleotide sequence of the 517 bp CsVMV promoter fragment is provided as SEQ ID NO:9. The 320 bp, 5' upstream promoter polynucleotide fragment is shown in italics font and is presented as SEQ ID NO:7. The 123 bp core promoter is shown in underlined font and is presented as SEQ ID NO:5. The 74 bp 5' UTR is shown in bold font and is presented as SEQ ID NO:6. Accordingly, SEQ ID NO:9 is provided as:

*CCAGAAGGTAATTATCCAAGATGTAGCATCAAGAATCCAATGTTTACGGG*

*AAAAACTATGGAAGTATTATGTGAGCTCAGCAAGAAGCAGATCAATATGC*

*GGCACATATGCAACCTATGTTCAAAAATGAAGAATGTACAGATACAAGAT*

*CCTATACTGCCAGAATACGAAGAAGAATACGTAGAAATTGAAAAAGAAGA*

*ACCAGGCGAAGAAAAGAATCTTGAAGACGTAAGCACTGACGACAACAATG*

*AAAAGAAGAAGATAAGGTCGGTGATTGTGAAAGAGACATAGAGGACACAT*

*GTAAGGTGGAAAATGTAAGGGCGGAAAGTAACCTTATCACAAAGGAATCT*

<u>TATCCCCCACTACTTATCCTTTTATATTTTTCCGTGTCATTTTTGCCCTT</u>

<u>GAGTTTTCCTATATAAGGAACCAAGTTCGGCATTTGTGAAAAC</u>AAGAAAA

AATTTGGTGTAAGCTATTTTCTTTGAAGTACTGAGGATACAACTTCAGAG

AAATTTGTAAGTTTGTA

Figure 2:
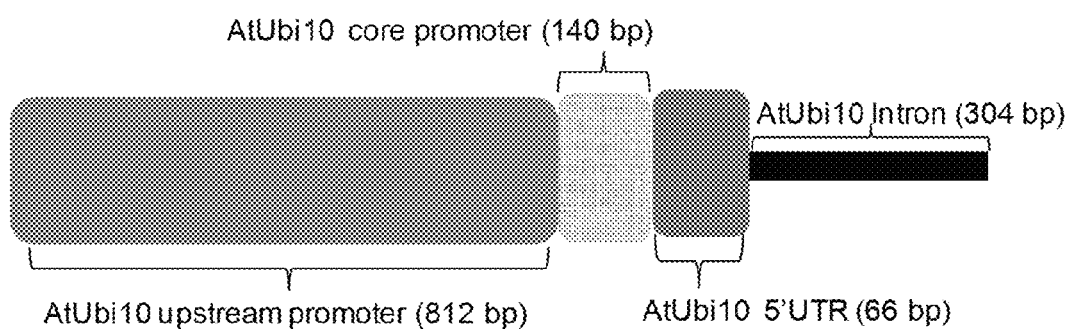

Example 2: Annotation of the *Arabidopsis thaliana* Ubiquitin 10 (AtUbi10) Promoter Elements The AtUbi10 promoter (SEQ ID NO:8; FIG. 2) is a 1,322 bp polynucleotide sequence (Callis, J., et al., (1995) Structure and evolution of genes encoding polyubiquitin and ubiquitin-like proteins in *Arabidopsis thaliana* ecotype columbia, *Genetics*, 139(2), 921-39). The polynucleotide sequence can be divided into three portions. The first portion is a 812 bp, 5' upstream promoter polynucleotide fragment (URS). The second portion is proximally located downstream of the 5' upstream portion. The second portion contains a 140 bp minimal core promoter (minUbi10P). The two portions are further attached to a third portion made up of an intron and 5' UTR. The 5' UTR is a 66 bp, 5' UnTranslated Region (UTR) which is located directly downstream of the 5' upstream promoter and the 140 bp core promoter. The 304 bp intron is located at the furthermost downstream end of the polynucleotide sequence.

The polynucleotide sequence of the 1,332 bp AtUbi10 promoter fragment is provided as SEQ ID NO:8. The 812 bp, 5' upstream promoter polynucleotide fragment is shown in italics font and is presented as SEQ ID NO:4. The 140 bp minimal core promoter is shown in underlined font and is presented as SEQ ID NO:1. The 66 bp 5' UTR is shown in bold font and is presented as SEQ ID NO:3. The 304 bp intron is shown in lower case font and is presented as SEQ ID NO:2. Accordingly SEQ ID NO:8 is provided as:

*GTCGACCTGCAGGTCAACGGATCAGGATATTCTTGTTTAAGATGTTGAAC*

*TCTATGGAGGTTTGTATGAACTGATGATCTAGGACCGGATAAGTTCCCTT*

*CTTCATAGCGAACTTATTCAAAGAATGTTTTGTGTATCATTCTTGTTACA*

*TTGTTATTAATGAAAAAATATTATTGGTCATTGGACTGAACACGAGTGTT*

*AAATATGGACCAGGCCCCAAATAAGATCCATTGATATATGAATTAAATAA*

*CAAGAATAAATCGAGTCACCAAACCACTTGCCTTTTTTAACGAGACTTGT*

*TCACCAACTTGATACAAAAGTCATTATCCTATGCAAATCAATAATCATAC*

*AAAAATATCCAATAACACTAAAAAATTAAAAGAAATGGATAATTTCACAA*

*TATGTTATACGATAAAGAAGTTACTTTTCCAAGAAATTCACTGATTTTAT*

*AAGCCCACTTGCATTAGATAAATGGCAAAAAAAAACAAAAAGGAAAAGAA*

*ATAAAGCACGAAGAATTCTAGAAAATACGAAATACGCTTCAATGCAGTGG*

*GACCCACGGTTCAATTATTGCCAATTTTCAGCTCCACCGTATATTTAAAA*

*AATAAAACGATAATGCTAAAAAAATATAAATCGTAACGATCGTTAAATCT*

*CAACGGCTGGATCTTATGACGACCGTTAGAAATTGTGGTTGTCGACGAGT*

*CAGTAATAAACGGCGTCAAAGTGGTTGCAGCCGGCACACACGAGTCGTGT*

*TTATCAACTCAAAGCACAAATACTTTTCCTCAACCTAAAAATAAGGCAAT*

*TAGCCAAAAACA*<u>ACTTTGCGTGTAAACAACGCTCAATACACGTGTCATTT</u>

<u>TATTATTAGCTATTGCTTCACCGCCTTAGCTTTCTCGTGACCTAGTCGTC</u>

<u>CTCGTCTTTTCTTCTTCTTCTATAAAACAATACCCAAAGCTTCTTCT</u>

T<u>C</u>ACAATTCAGATTTCAATTTCTCAAAATCTTAAAAACTTTCTCTCAATT

CTCTCTACCGTGATCAAGgtaaatttctgtgttccttattctctcaaaat cttcgatttgttttcgttcgatcccaatttcgtatatgttctttggttt agattctgttaatcttagatcgaagacgattttctgggtttgatcgttag atatcatcttaattctcgattagggtttcataaatatcatccgatttgtt caaataatttgagttttgtcgaataattactcttcgatttgtgatttcta tctagatctggtgttagtttctagtttgtgcgatcgaatttgtcgattaa tctgagtttttctgattaacag Example 3: Design of Bi-Directional Promoters A first bi-directional promoter that contained gene regulatory elements from the CsVMV and AtUbi10 promoters was designed and is presented as SEQ ID NO:10. This bi-directional promoter contains sequence of the partial CsVMV promoter (base pairs 1-197) fused in reverse complimentary orientation to the 5' end of the full length AtUbi10 promoter (base pairs 198-1,519). The components of the partial CsVMV promoter contain a 123 bp region of the CsVMV minimal core promoter (underlined font at base pairs 75-197; SEQ ID NO:5), and the CsVMV 5' untranslated region (bold font at base pairs 1-74; SEQ ID NO:6). The components of the full length AtUbi10 promoter contain an upstream promoter region (italics font at base pairs 198-1009; SEQ ID NO:4), AtUbi10 minimal core promoter (double underlined font at base pairs 1,010-1,149; SEQ ID NO:1), the AtUbi10 5' untranslated region (bold and underlined font at base pairs 1,150-1,215; SEQ ID NO:3) and the AtUbi10 intron (lower case font at base pairs 1,216-1519; SEQ ID NO:2). Accordingly SEQ ID NO:10 is provided as:

TACAAACTTACAAATTTCTCTGAAGTTGTATCCTCAGTACTTCAAAGAAA

ATAGCTTACACCAAATTTTTTCTT<u>GTTTTCACAAATGCCGAACTTGGTTC</u>

<u>CTTATATAGGAAAACTCAAGGGCAAAAATGACACGGAAAAATATAAAAGG</u>

<u>ATAAGTAGTGGGGGATAAGATTCCTTTGTGATAAGGTTACTTTCCGCGTC</u>

*GACCTGCAGGTCAACGGATCAGGATATTCTTGTTTAAGATGTTGAACTCT*

*ATGGAGGTTTGTATGAACTGATGATCTAGGACCGGATAAGTTCCCTTCTT*

*CATAGCGAACTTATTCAAAGAATGTTTTGTGTATCATTCTTGTTACATTG*

*TTATTAATGAAAAAATATTATTGGTCATTGGACTGAACACGAGTGTTAAA*

*TATGGACCAGGCCCCAAATAAGATCCATTGATATATGAATTAAATAACAA*

*GAATAAATCGAGTCACCAAACCACTTGCCTTTTTTAACGAGACTTGTTCA*

*CCAACTTGATACAAAAGTCATTATCCTATGCAAATCAATAATCATACAAA*

*AATATCCAATAACACTAAAAAATTAAAAGAAATGGATAATTTCACAATAT*

*GTTATACGATAAAGAAGTTACTTTTCCAAGAAATTCACTGATTTTATAAG*

*CCCACTTGCATTAGATAAATGGCAAAAAAAAACAAAAAGGAAAAGAAATA*

*AAGCACGAAGAATTCTAGAAAATACGAAATACGCTTCAATGCAGTGGGAC*

*CCACGGTTCAATTATTGCCAATTTTCAGCTCCACCGTATATTTAAAAAAT*

*AAAAACGATAATGCTAAAAAAATATAAATCGTAACGATCGTTAAATCTCAA*

*CGGCTGGATCTTATGACGACCGTTAGAAATTGTGGTTGTCGACGAGTCAG*

*TAATAAACGGCGTCAAAGTGGTTGCAGCCGGCACACACGAGTCGTGTTTA*

*TCAACTCAAAGCACAAATACTTTTCCTCAACCTAAAAATAAGGCAATTAG*

*CCAAAAACA*<u>ACTTTGCGTGTAAACAACGCTCAATACACGTGTCATTTTAT</u>

<u>TATTAGCTATTGCTTCACCGCCTTAGCTTTCTCGTGACCTAGTCGTCCTC</u>

<u>GTCTTTTCTTCTTCTTCTATAAAACAATACCCAAAGCTTCTTCTTCA</u>

CAATTCAGATTTCAATTTCTCAAAATCTTAAAAACTTTCTCTCAATTCTC

TCTACCGTGATCAAGgtaaatttctgtgttccttattctctcaaaatctt cgattttgttttcgttcgatcccaatttcgtatatgttctttggtttaga ttctgttaatcttagatcgaagacgattttctgggtttgatcgttagata tcatcttaattctcgattagggtttcataaatatcatccgatttgttcaa ataatttgagttttgtcgaataattactcttcgatttgtgatttctatct agatctggtgttagtttctagtttgtgcgatcgaatttgtcgattaatct gagttttctgattaacag A second bi-directional promoter that contained gene regulatory elements from the AtUbi10 promoter was designed and is presented as SEQ ID NO:11. This bi-directional promoter contains a partial sequence of the AtUbi10 promoter (base pairs 1-510) fused in reverse complimentary orientation to the 5' end of the full length AtUbi10 promoter (base pairs 511-1,832; SEQ ID NO:4). The components of the partial AtUbi10 promoter contain a 140 bp region of the AtUbi10 minimal core promoter (underlined font, base pairs 371-510; SEQ ID NO:1), the AtUbi10 5' untranslated region (bold font, base pairs 305-370; SEQ ID NO:3), and the AtUbi10 intron (lower case font, base pairs 1-304; SEQ ID NO:2). The components of the full-length AtUbi10 promoter contain the upstream promoter region (italics font, base pairs 511-1,322; SEQ ID NO:4), AtUbi10 minimal core promoter (double underlined font, base pairs 1,323-1,462; SEQ ID NO:1), the AtUbi10 5' untranslated region (bold and underlined font, base pairs 1,463-1,528; SEQ ID NO:3), and the AtUbi10 intron (lower case and underlined font, base pairs 1,529-1,832; SEQ ID NO:2). Accordingly SEQ ID NO:11 is provided as:

ctgttaatcagaaaaactcagattaatcgacaaattcgatcgcacaaact agaaactaacaccagatctagatagaaatcacaaatcgaagagtaattat tcgacaaaactcaaattatttgaacaaatcggatgatatttatgaaaccc taatcgagaattaagatgatatctaacgatcaaacccagaaaatcgtctt cgatctaagattaacagaatctaaaccaaagaacatatacgaaattggga tcgaacgaaaacaaaatcgaagattttgagagaataaggaacacagaaat ttacCTTGATCACGGTAGAGAGAATTGAGAGAAAGTTTTTAAGATTTTGA

GAAATTGAAATCTGAATTGTGAAGAAGAAGCTTTGGGTATTGTTTTATAG

AAGAAGAAGAAGAAAGACGAGGACGACTAGGTCACGAGAAAGCTAAGGC

GGTGAAGCAATAGCTAATAATAAAATGACACGTGTATTGAGCGTTGTTTA

CACGCAAAGTGTCGACCTGCAGGTCAACGGATCAGGATATTCTTGTTTAA

GATGTTGAACTCTATGGAGGTTTGTATGAACTGATGATCTAGGACCGGAT

AAGTTCCCTTCTTCATAGCGAACTTATTCAAAGAATGTTTTGTGTATCAT

TCTTGTTACATTGTTATTAATGAAAAAATATTATTGGTCATTGGACTGAA

CACGAGTGTTAAATATGGACCAGGCCCCAAATAAGATCCATTGATATATG

AATTAAATAACAAGAATAAATCGAGTCACCAAACCACTTGCCTTTTTTAA

CGAGACTTGTTCACCAACTTGATACAAAAGTCATTATCCTATGCAAATCA

ATAATCATACAAAAATATCCAATAACACTAAAAAATTAAAAGAAATGGAT

AATTTCACAATATGTTATACGATAAAGAAGTTACTTTTCCAAGAAATTCA

CTGATTTTATAAGCCCACTTGCATTAGATAAATGGCAAAAAAAAACAAAA

AGGAAAAGAAATAAAGCACGAAGAATTCTAGAAAATACGAAATACGCTTC

AATGCAGTGGGACCCACGGTTCAATTATTGCCAATTTTCAGCTCCACCGT

ATATTTAAAAAATAAAACGATAATGCTAAAAAAATATAAATCGTAACGAT

CGTTAAATCTCAACGGCTGGATCTTATGACGACCGTTAGAAATTGTGGTT

GTCGACGAGTCAGTAATAAACGGCGTCAAAGTGGTTGCAGCCGGCACACA

CGAGTCGTGTTTATCAACTCAAAGCACAAATACTTTTCCTCAACCTAAAA

ATAAGGCAATTAGCCAAAAACAACTTTGCGTGTAAACAACGCTCAATACA

CGTGTCATTTTATTATTAGCTATTGCTTCACCGCCTTAGCTTTCTCGTGA

CCTAGTCGTCCTCGTCTTTTCTTCTTCTTCTTCTATAAAACAATACCCAA

AGCTTCTTCTTCACAATTCAGATTTCAATTTCTCAAAATCTTAAAAACTT

TCTCTCAATTCTCTCTACCGTGATCAAGgtaaatttctgtgttccttatt ctctcaaaatcttcgatttgttttcgttcgatcccaatttcgtatatgt tctttggtttagattctgttaatcttagatcgaagacgattttctgggtt tgatcgttagatatcatcttaattctcgattagggtttcataaatatcat ccgatttgttcaaataatttgagttttgtcgaataattactcttcgattt gtgatttctatctagatctggtgttagtttctagtttgtgcgatcgaatt tgtcgattaatctgagttttctgattaacag A third bi-directional promoter that contained gene regulatory elements from the CsVMV and AtUbi10 promoters was designed and is presented as SEQ ID NO:12. This bi-directional promoter contains sequence of the partial AtUbi10 promoter (base pairs 1-510) fused in reverse complimentary orientation to the 5' end of the full-length CsVMV promoter (base pairs 511-1,027). The components of the partial AtUbi10 promoter contain a 140 bp region of the AtUbi10 minimal core promoter (underlined font, base pairs 371-510; SEQ ID NO:1), the AtUbi10 5' untranslated region (bold font, base pairs 305-370; SEQ ID NO:3), and the AtUbi10 intron (lower case font, base pairs 1-304; SEQ ID NO:2). The components of the CsVMV promoter contain the upstream promoter region (italics font, base pairs 511-830; SEQ ID NO:7), CsVMV minimal core promoter (double underlined font, base pairs 831-953; SEQ ID NO:5), and the CsVMV 5' untranslated region (bold and underlined font, base pairs 954-1,027; SEQ ID NO:6). Accordingly SEQ ID NO:12 is provided as:

ctgttaatcagaaaaactcagattaatcgacaaattcgatcgcacaaact agaaactaacaccagatctagatagaaatcacaaatcgaagagtaattat tcgacaaaactcaaattatttgaacaaatcggatgatatttatgaaaccc taatcgagaattaagatgatatctaacgatcaaacccagaaaatcgtctt cgatctaagattaacagaatctaaaccaaagaacatatacgaaattggga tcgaacgaaaacaaaatcgaagattttgagagaataaggaacacagaaat ttacCTTGATCACGGTAGAGAGAATTGAGAGAAAGTTTTTAAGATTTTGA

GAAATTGAAATCTGAATTGTGAAGAAGAAGCTTTGGGTATTGTTTTATAG

```
AAGAAGAAGAAGAAAAGACGAGGACGACTAGGTCACGAGAAAGCTAAGGC

GGTGAAGCAATAGCTAATAATAAAATGACACGTGTATTGAGCGTTGTTTA

CACGCAAAGTCCAGAAGGTAATTATCCAAGATGTAGCATCAAGAATCCAA

TGTTTACGGGAAAAACTATGGAAGTATTATGTGAGCTCAGCAAGAAGCAG

ATCAATATGCGGCACATATGCAACCTATGTTCAAAAATGAAGAATGTACA

GATACAAGATCCTATACTGCCAGAATACGAAGAAGAATACGTAGAAATTG

AAAAAGAAGAACCAGGCGAAGAAAAGAATCTTGAAGACGTAAGCACTGAC

GACAACAATGAAAAGAAGAAGATAAGGTCGGTGATTGTGAAAGAGACATA

GAGGACACATGTAAGGTGGAAAATGTAAGGGCGGAAAGTAACCTTATCAC

AAAGGAATCTTATCCCCCACTACTTATCCTTTTATATTTTTCCGTGTCAT

TTTTGCCCTTGAGTTTTCCTATATAAGGAACCAAGTTCGGCATTTGTGAA

AACAAGAAAAAATTTGGTGTAAGCTATTTTCTTTGAAGTACTGAGGATAC

AACTTCAGAGAAATTTGTAAGTTTGTA
```

A fourth bi-directional promoter that contained gene regulatory elements from the CsVMV promoter was designed and is presented as SEQ ID NO:13. This bi-directional promoter contains a partial sequence of the CsVMV promoter (base pairs 1-197) fused in reverse complimentary orientation to the 5' end of the full length CsVMV promoter (base pairs 198-714). The components of the partial CsVMV promoter contain the 123 bp region of CsVMV minimal core promoter (underlined font, base pairs 75-197; SEQ ID NO:5), and the CsVMV 5' untranslated region (bold font, base pairs 1-74; SEQ ID NO:6). The components of the full-length CsVMV promoter contain the upstream promoter region (italics font, base pairs 198-518; SEQ ID NO:7), CsVMV core promoter (double underlined font, base pairs 519-640; SEQ ID NO:5), and the CsVMV 5' untranslated region (bold and underlined font, base pairs 641-714; SEQ ID NO:6). Accordingly SEQ ID NO:13 is provided as:

```
TACAAACTTACAAATTTCTCTGAAGTTGTATCCTCAGTACTTCAAAGAAA

ATAGCTTACACCAAATTTTTTCTTGTTTTCACAAATGCCGAACTTGGTTC

CTTATATAGGAAAACTCAAGGGCAAAAATGACACGGAAAAATATAAAAGG

ATAAGTAGTGGGGATAAGATTCCTTTGTGATAAGGTTACTTTCCGCCCA

GAAGGTAATTATCCAAGATGTAGCATCAAGAATCCAATGTTTACGGGAAA

AACTATGGAAGTATTATGTGAGCTCAGCAAGAAGCAGATCAATATGCGGC

ACATATGCAACCTATGTTCAAAAATGAAGAATGTACAGATACAAGATCCT

ATACTGCCAGAATACGAAGAAGAATACGTAGAAATTGAAAAAGAAGAACC

AGGCGAAGAAAAGAATCTTGAAGACGTAAGCACTGACGACAACAATGAAA

AGAAGAAGATAAGGTCGGTGATTGTGAAAGAGACATAGAGGACACATGTA

AGGTGGAAAATGTAAGGGCGGAAAGTAACCTTATCACAAAGGAATCTTAT

CCCCCACTACTTATCCTTTTATATTTTTCCGTGTCATTTTTGCCCTTGAG

TTTTCCTATATAAGGAACCAAGTTCGGCATTTGTGAAACAAGAAAAAAT

TTGGTGTAAGCTATTTTCTTTGAAGTACTGAGGATACAACTTCAGAGAAA

TTTGTAAGTTTGTA
```

Example 4: Plant Transformation Constructs

Plant transformation constructs were designed to test the expression of the bi-directional promoters in planta. The final bi-directional promoter constructs were generated by inserting a minimal promoter driving one reporter gene upstream and in reverse complimentary orientation of the primary promoter driving the second reporter gene. Eight plasmids, pDAB113192, pDAB113193, pDAB113194, pDAB113195, pDAB113196, pDAB113197, pDAB113198, and pDAB113199 were built to contain gene regulatory elements from the CsVMV and AtUbi10 promoters driving both the green fluorescent protein (gfp; Evrogen, Moscow, Russia) and red fluorescent protein (rfp; Clontech, Mountain View, Calif.) transgenes and terminated by either the *Agrobacterium tumefaciens* ORF 23/24 3' UTR (Barker et al, *Plant Molecular Biology* 1983, 2(6), 335-50) or the *Agrobacterium tumefaciens* Nopaline synthase 3' UTR (Table 1). The resulting constructs contained a single bi-directional promoter that drove two different transgenes which were operably linked to the 5' and 3' end of the bi-directional promoter. The constructs were assembled using an In-Fusion® cloning process, which necessitated the addition of 15-20 bp homologies to the appropriate fragment ends to allow for proper fragment alignment during cloning. The plant expression constructs were cloned into a pEntry11™ linear backbone (Life Technologies, Carlsbad, Calif.). Fragments were amplified using High Fidelity PHUSION® PCR (New England Biolabs, Ipswich, Mass.). The IN-Fusion® HD EcoDry™ cloning system (Life Technologies) was utilized, and colonies were selected for on LB (50 μg/ml kanamycin) media. Plasmid constructs were confirmed using mini-prep and maxi-prep DNA extraction with a Qiagen MINIPREP SPIN KIT™ (Qiagen, Valencia, Calif.) and Qiagen ENDOFREE® Plasmid Maxi Kit (Qiagen).

TABLE 1

Description of constructs containing the bi-directional promoters which were constructed to drive expression of the rfp and gfp transgenes (e.g., pDAB113192-113199).

| pDAB | CONSTRUCTS | | | | SEQ ID NO: |
|---|---|---|---|---|---|
| Control Constructs | | | | | |
| 113190 | CsVMV promoter v1 | RFPv2 | AtuORF23 3' UTR v1 | | 14 |

TABLE 1-continued

Description of constructs containing the bi-directional promoters which were constructed to drive expression of the rfp and gfp transgenes (e.g., pDAB113192-113199).

CONSTRUCTS

| pDAB | | | | | | SEQ ID NO: |
|---|---|---|---|---|---|---|
| 113188 | CsVMV promoter v1 | Turbo GFP v2 | AtuNos 3' UTR v2 | | | 15 |
| Bi-directional Promoter Constructs | | | | | | |
| 113192 | AtuORF 23 3' UTR v1 | RFPv2 | AtUbi10 bi-directional promoter with additional AtUbi10 promoter elements of SEQ ID NO: 11 | Turbo GFP v2 | AtuNos 3' UTR v2 | 16 |
| 113193 | AtuNos 3' UTR v2 | Turbo GFP v2 | AtUbi10 bi-directional promoter with additional AtUbi10 promoter elements of SEQ ID NO: 11 | RFPv2 | AtuORF23 3' UTR v1 | 17 |
| 113194 | AtuORF 23 3' UTR v1 | RFPv2 | AtUbi10 bi-directional promoter with additional CsVMV promoter elements of SEQ ID NO: 10 | Turbo GFP v2 | AtuNos 3' UTR v2 | 18 |
| 113195 | AtuNos 3' UTR v2 | Turbo GFP v2 | AtUbi10 bi-directional promoter with additional CsVMV promoter elements of SEQ ID NO: 10 | RFPv2 | AtuORF23 3' UTR v1 | 19 |
| 113196 | AtuORF 23 3' UTR v1 | RFPv2 | CsVMV bi-directional promoter with additional AtUbi10 promoter elements of SEQ ID NO: 12 | Turbo GFP v2 | AtuNos 3' UTR v2 | 20 |
| 113197 | AtuNos 3' UTR v2 | Turbo GFP v2 | CsVMV bi-directional promoter with additional AtUbi10 promoter elements of SEQ ID NO: 12 | RFPv2 | AtuORF23 3' UTR v1 | 21 |
| 113198 | AtuORF 23 3' UTR v1 | RFPv2 | CsVMV bi-directional promoter with additional CsVMV promoter elements of SEQ ID NO: 13 | Turbo GFP v2 | AtuNos 3' UTR v2 | 22 |
| 113199 | AtuNos 3' UTR v2 | Turbo GFP v2 | CsVMV bi-directional promoter with additional CsVMV promoter elements of SEQ ID NO: 13 | RFPv2 | AtuORF23 3' UTR v1 | 23 |

Example 5: Soybean Plant Transformation

The above described constructs were used to transform soybean plants. The soybeans plants (*Glycine max* c.v. Maverick) were planted in a greenhouse and cultivated under a 12/12 Day/Night photoperiod with an 80-86° F. temperature. Five weeks after planting (which is around 7 to 14 days after flowering) soybean pods larger than 0.9 cm in width were harvested.

The harvested pods were surface sterilized by washing the pods with 70% ethanol for 30 seconds followed by a 10 minute wash with 10% bleach containing 2 drops of TWEEN®-20 with gentle agitation. The bleach was decanted and the explants were rinsed 3 times with sterile water for 5 minutes each with gentle agitation. Sterile pods were stored at 4° C. for 7-8 days.

The positions of the immature embryos within the pods were determined by backlighting the pods on a transilluminated stereoscope. Embryos of 3 mm to 5 mm in length were used for transformation, and oversize or undersize embryos were discarded. Two cuts were made on both ends of pod and one cut along the longitudinal curved part of the pod was made. While making the longitudinal cut, enough plant tissue was cut away to expose the interior of the pod cavity. The pod was then opened and the immature embryos were removed. Isolated embryos were placed on plasmolysis media (4.4 g/L MS basal with vitamins (M519), 73 g/L mannitol, 73 g/L sorbitol, 2.3 g/L gelzan (GEL-RITE®), 1 g/L magnesium chloride) for four hours prior to bombardment.

Gold microcarriers were prepared in a siliconized 2 ml tube. About 50 mg of 0.6 μm gold microcarriers (Bio-Rad, Hercules, Calif.) and 1 ml of 100% ethanol were added and vortexed for 2 minutes. This step was followed by centrifugation at 1,000×g for 4 minutes, discarding the supernatant. Next, 1 ml of 70% ethanol was added, vortexed for 2 minutes, then the tube was incubated for 15 minutes at room temperature with occasionally vortexing. After incubation, the preparation was centrifuged for 1 minute at 1000×g, discarding the supernatant. The particles were rinsed by adding 1 ml of sterile water with vortexing for 1 minute, allowing the particles to settle for 1 minute, then centrifuging at 1800×g for 1 minute. The washing step was repeated two additional times. The resulting pellet plant material was resuspended in 50% sterile glycerol.

Prepared gold microcarriers were coated with DNA for bombardment by first resuspending via vortexing for 2 minutes and transferring the 50 μl solution into a siliconized tube. While vortexing the tube, reagents were added in the following order: 5 μl of DNA, 50 μl of 2.5 M CaCl, and 20 μl of 0.1 M spermidine. The tube was capped and vortexed at 4° C. for 20 minutes. After vortexing, 200 μl of 100% ethanol was added, vortexed for 1 minute, and centrifuged at 1000×g for 1 minute. Supernatant was removed and the ethanol wash was repeated two more times. The final pellet was resuspended in 50 μl of 100% ethanol.

At the time of bombardment, 9 μl of vortexed DNA/gold microcarrier mixture was spread in an even coat over the center of the macrocarrier positioned in the macrocarrier holder, this step was repeated until all the bombardment macrocarriers were coated. Immature embryos were oriented on plasmolysis media so that the abaxial side was face up and centered in the plate. Samples were bombarded with Biorad PDS-1000/HE™ gene gun using 900 psi rupture disks at 9 cm from the target. Embryos were transferred to SE40 media (4.3 g/L MS basal salt (M524), 1 ml/L Gamborg B5 vitamins (G249), 30 g/L sucrose, 4 ml/L 2,4-D 10 mg/ml, 2 g/L GELRITE®).

The bombarded soybean plant material was imaged for 24 to 48 hours after bombardment on a Leica M165FC™ stereo scope with DFC310FX camera (Leica, Wetzlar, Germany) using the RFP and GFP filter set. Images were split using ImageJ™ (W. S. Rasband, ImageJ, U.S. National Institutes of Health, Bethesda, Md., USA, on the internet at image-j.nih.gov/ij/, 1997-2014) into red, green, and blue channels, with the analyzed channel being chosen for by selecting the best channel that presented foci. The threshold was optimized to determine the total area using the wand tracing tool. Foci were quantitated using Find Maxima function in ImageJ™. Background foci were subtracted from experimental totals using unbombarded and bombarded plant material without DNA controls plates.

Example 6: Transient Gene Expression in Soybean

Soybean immature embryos were transformed using particle bombardment as described above. After the bombardment, the plant material were incubated from 24-48 hours and the samples were visualized (FIG. 3) using Leica M165 FC™ stereo scope with DFC310FX camera and analyzed for foci count using ImageJ™ (FIG. 4 and Table 2).

TABLE 2

Relative fluorescent intensity in soybean.

| Construct | GFP-Normalized | RFP-Normalized |
| --- | --- | --- |
| pDAB113188 | 159.2485878 | −25.94461673 |
| pDAB113190 | −188.8269798 | 2040.118661 |
| pDAB113192 | 1076.365219 | 2161.898374 |
| pDAB113194 | 744.6226674 | 2563.785683 |
| pDAB113198 | 325.6486152 | 1320.688037 |
| pDAB113199 | 3.74352145 | 1640.502692 |

Figure 3:
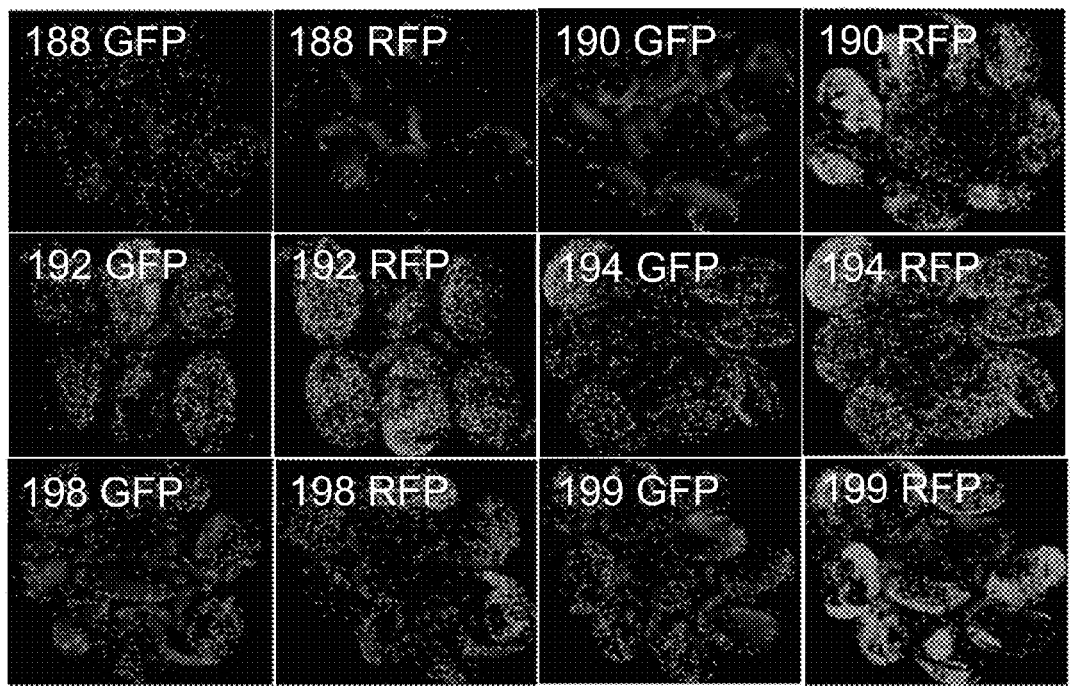
Figure 4:
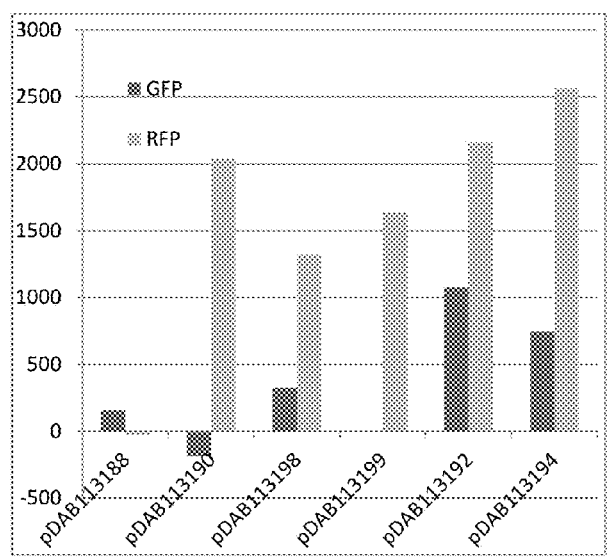

The microscopy images provided in FIG. 3 and the quantitated proteins expression levels provided in FIG. 4 and Table 2 indicate that the bi-directional promoters containing the CsVMV and AtUbi10 gene regulatory elements of pDAB113198 (bi-directional promoter of SEQ ID NO:13), pDAB113199 (bi-directional promoter of SEQ ID NO:13), pDAB113192 (bi-directional promoter of SEQ ID NO:11), and pDAB113194 (bi-directional promoter of SEQ ID NO:10) drove expression of both the GFP & RFP proteins. The expression levels of the bi-directional promoters are comparable to the single promoter controls that drove expression of either GFP (pDAB113188) or RFP (pDAB113190). In addition, the bi-directional promoters of pDAB113198, pDAB113192, and pDAB113194 drove expression of GFP at comparable levels as compared to the control construct pDAB113188.

Example 7: Maize Transformation

The above described constructs were used to transform maize cells. Immature maize embryos were obtained from Zea mays (c.v. B104) grown in the greenhouse. The maize plants were self or sib-pollinated, and the ears were harvested 9-12 days post-pollination. The day before the experiment, ears were surface-sterilized by immersion in a 20% solution of household bleach, which contained 5% sodium hypochlorite, and shaken for 20-30 minutes, followed by three rinses in sterile water. After sterilization, immature zygotic embryos (size 2.0-2.4 mm) were aseptically dissected from each ear and collected in 2 ml tubes containing osmotic medium. Upon completion of isolation, the osmotic medium was removed, and embryos were randomly transferred onto semi-solid osmotic medium. The embryos were arranged in appropriate target format for biolistic transformation. Plates were incubated overnight in a continual 50 µM low light chamber at 27.5° C.

On the day of the experiment, sterilized gold microcarriers were prepared for transformation by thawing gold mirocarriers on ice, vortexing, and aliquoting 50 µl of suspended gold into a sterilized 2 ml tube. While vortexing the following components were added in order; gold microcarrier, 5 µl of 1.0 µg/µl stock, 50 µl of 2.5 M CaCl$_2$, and 20 µl of 0.1 M spermidine. The resulting suspension was vortexed at 4° C. for 20 minutes, washed three times with ethanol, and resuspended in 30 µl of 100% ethanol. The prepared suspension was stored on ice until bombardment.

At the time of bombardment, macrocarriers were prepared by evenly spreading 5 µl of vortexed DNA/gold microcarrier mixture on the center of the macrocarrier, this step was repeated for each sample, and the complex was allowed to dry for about 10 minutes. Bombardment was done using a Biorad Biolistic PDS-1000/He Particle Delivery System™ at 6 cm using sterilized 900 psi rupture discs.

After bombardment, plates were wrapped with 3 M Tape™ and stored on a tray in continuous, 50 µM low light conditions at 27.5° C. overnight. After 24 hours, transient expression was observed using the Typhoon Imaging System™ (GE Healthcare, Little Chalfont, Buckinghamshire, United Kingdom).

Example 8: Transient Gene Expression in Maize

Figure 5:
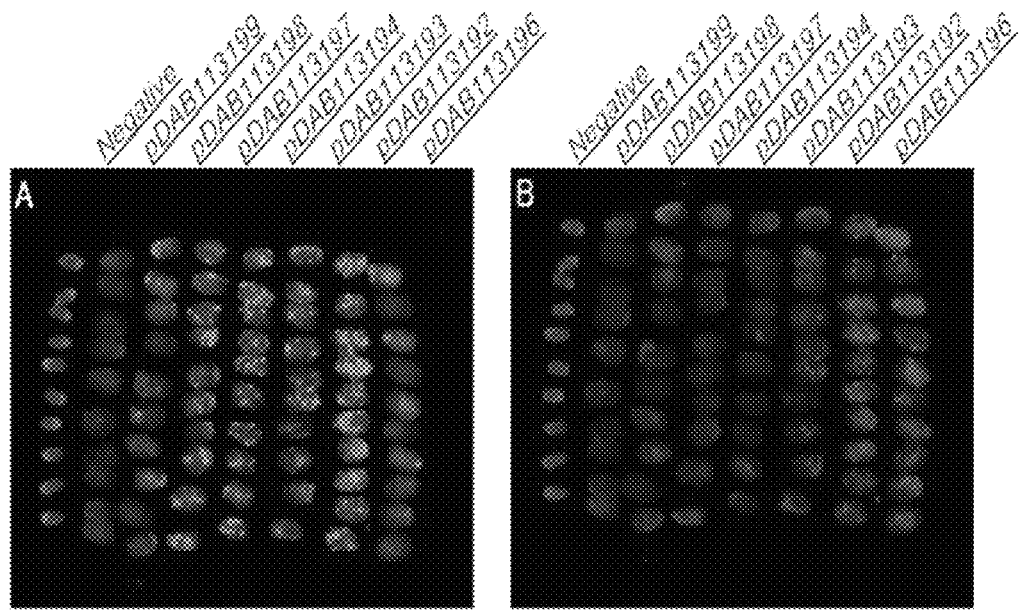
Figure 6:
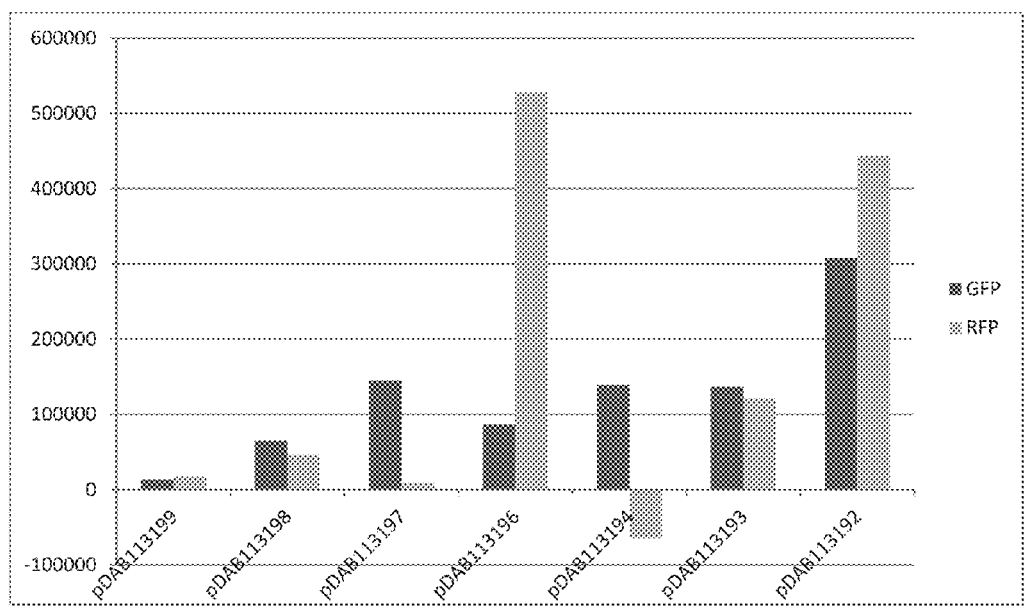

Maize immature embryos were transformed using the particle bombardment as described above. After 24 hours of incubation, samples were visualized using the Typhoon Imager System™ (FIG. 5). The microscopy images provided in FIG. 5 and the quantitated proteins expression levels provided in FIG. 6 and Table 3 indicate that the bi-directional promoters containing the CsVMV and AtUbi10 gene regulatory elements of pDAB113198 (bi-directional promoter of SEQ ID NO:13), pDAB113199 (bi-directional promoter of SEQ ID NO:13), pDAB113192 (bi-directional promoter of SEQ ID NO:11), pDAB113194 (bi-directional promoter of SEQ ID NO:10), pDAB113193 (bi-directional promoter of SEQ ID NO:11), pDAB113196 (bi-directional promoter of SEQ ID NO:12), and pDAB113197 (bi-directional promoter of SEQ ID NO:12) drove expression of both the GFP & RFP proteins. The expression data further suggest that the AtUbi10 minimal promoter coupled with either CsVMV or AtUbi10 polar promoter gives high expression of the transgene in the opposite orientation. In comparison, CsVMV minimal promoter showed a relatively lower expression (FIG. 6). The expression levels of the bi-directional promoters for expression of either GFP or RFP were quantitated. As shown in FIG. 5, the bi-directional promoters of pDAB113199, pDAB113198, pDAB113197, pDAB113196, pDAB113194, pDAB113193 and pDAB113192 drove expression of GFP at high levels of expression. In addition, the bi-directional promoters of pDAB113199, pDAB113198, pDAB113197, pDAB113196, pDAB113193 and pDAB113192 drove expression of RFP at high levels of expression.

TABLE 3

Relative fluorescent intensity in maize.

| Construct | GFP-Normalized | RFP-Normalized |
|---|---|---|
| pDAB113199 | 13176.8 | 17,122 |
| pDAB113198 | 64987.96 | 46,414 |
| pDAB113197 | 145055.79 | 9,575 |
| pDAB113194 | 138988.03 | −64,323 |
| pDAB113193 | 136832.49 | 121,645 |
| pDAB113192 | 308049.47 | 443,347 |
| pDAB113196 | 86714.18 | 527,405 |

In summary, the AtUbi10 and CsVMV promoters have been converted into novel synthetic CsVMV bi-directional promoters comprising a plurality of promoter elements from an *Arabidopsis thaliana* Ubiquitin-10 promoter and a Cassava Vein Mosaic Virus promoter that are functional both in soybean and corn. The expression levels of the first and second nucleotides of interest obtained from bi-directional promoter appears to be comparable to unidirectional promoter gene constructs. The bi-directional promoters robustly drive expression of multiple transgene sequences that are fused onto either end of the bi-directional promoter.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A nucleic acid molecule comprising a bidirectional promoter selected from the group consisting of SEQ ID NO:10, SEQ ID NO:11, SEQ ID NO:12, and SEQ ID NO:13.

2. The nucleic acid molecule of claim 1, wherein the bidirectional promoter is SEQ ID NO:10.

3. The nucleic acid molecule of claim 1, wherein the bidirectional promoter is SEQ ID NO:11.

4. The nucleic acid molecule of claim 1, wherein the bidirectional promoter is SEQ ID NO:12.

5. The nucleic acid molecule of claim 1, wherein the bidirectional promoter is SEQ ID NO:13.

6. The nucleic acid molecule of claim 1, further comprising a first polynucleotide encoding a polypeptide of interest operably linked to the 3' end of the bidirectional promoter.

7. The nucleic acid molecule of claim 6, further comprising a second polynucleotide encoding a polypeptide of interest operably linked to the 5' end of the bidirectional promoter.

8. The nucleic acid molecule of claim 6, wherein the polypeptide of interest is involved in a plant trait.

9. The nucleic acid molecule of claim 8, wherein the plant trait is selected from the group consisting of insect resistance, herbicide tolerance, nitrogen use efficiency, water use efficiency, and nutritional quality.

10. A method for producing a transgenic plant cell, the method comprising:
transforming a plant cell with the nucleic acid molecule of claim 1, wherein the nucleic acid molecule further comprises at least one polynucleotide encoding a polypeptide of interest operably linked to the bidirectional promoter, thereby producing a transgenic plant cell.

11. The method according to claim 10, wherein the plant cell is comprised in a plant, plant part, plant cell culture, or plant tissue culture.

12. The method according to claim 10, wherein the plant cell is transformed by a transformation method selected from the group consisting of *Agrobacterium*-mediated transformation, biolistics transformation, silicon carbide transformation, protoplast transformation, and liposome transformation.

13. The method according to claim 10, the method further comprising:
regenerating a transgenic plant from the transgenic plant cell.

14. The method according to claim 10, wherein the plant cell is selected from the group consisting of *Arabidopsis*, tobacco, soybean, canola, cotton, maize, rice, *Brachypodium*, and wheat.

15. A transgenic plant cell comprising an expression cassette that comprises a bidirectional promoter selected from the group consisting of SEQ ID NO:10, SEQ ID NO:11, SEQ ID NO:12, and SEQ ID NO:13 operably linked to a polynucleotide encoding a polypeptide of interest.

16. The transgenic plant cell of claim 15, wherein the expression cassette is stably integrated in the genome of the cell.

17. The transgenic plant cell of claim 16, wherein the polypeptide of interest is involved in an agronomic trait.

18. The transgenic plant cell of claim 17, wherein the agronomic trait is selected from the group consisting of insect resistance, herbicide tolerance, nitrogen use efficiency, water use efficiency, and nutritional quality.

19. The transgenic plant cell of claim 17, wherein the agronomic trait is herbicide tolerance.

20. The transgenic plant cell of claim 19, wherein the polynucleotide comprises aad-1.

21. A transgenic plant commodity product comprising the nucleic acid molecule of claim 1.

22. The transgenic plant commodity product of claim 21, wherein the commodity product is selected from the group consisting of grain, meal, flour, oil, or fiber.

23. The transgenic plant cell of claim 15, wherein the transgenic plant cell is from a plant selected from the group consisting of *Arabidopsis*, tobacco, soybean, canola, cotton, maize, rice, *Brachypodium*, and wheat.

24. The transgenic plant cell of claim 23, wherein the transgenic plant cell is a soybean cell.

25. The nucleic acid molecule of claim 1, further comprising a first polynucleotide encoding a polypeptide of interest operably linked to the 5' end of the bidirectional promoter.

26. The nucleic acid molecule of claim 25, wherein the polypeptide of interest is involved in a plant trait.

27. The nucleic acid molecule of claim 26, wherein the plant trait is selected from the group consisting of insect resistance, herbicide tolerance, nitrogen use efficiency, water use efficiency, and nutritional quality.

28. The transgenic plant cell of claim 15, wherein the polynucleotide encoding the polypeptide of interest is constitutively expressed.

29. The transgenic plant cell of claim 15, further comprising a second polynucleotide encoding a polypeptide of interest operably linked to the other end of the bidirectional promoter from the first polynucleotide.

30. The transgenic plant cell of claim 29, wherein the transgenic plant cell is from a plant selected from the group consisting of *Arabidopsis*, tobacco, soybean, canola, cotton, maize, rice, *Brachypodium*, and wheat.

31. A transgenic plant or seed comprising an expression cassette that comprises a bidirectional promoter selected from the group consisting of SEQ ID NO:10, SEQ ID NO:11, SEQ ID NO:12, and SEQ ID NO:13 operably linked to a polynucleotide encoding a polypeptide of interest.

32. The transgenic plant or seed of claim 31, wherein the polypeptide of interest is involved in an agronomic trait.

33. The transgenic plant or seed of claim 32, wherein the agronomic trait is selected from the group consisting of insect resistance, herbicide tolerance, nitrogen use efficiency, water use efficiency, and nutritional quality.

34. The transgenic plant or seed of claim 31, wherein the plant or seed is a monocotyledonous plant or seed.

35. The transgenic plant or seed of claim 31, wherein the plant or seed is a dicotyledonous plant or seed.

36. The transgenic plant or seed of claim 31, wherein the transgenic plant or seed is selected from the group consisting of *Arabidopsis*, tobacco, soybean, canola, cotton, maize, rice, *Brachypodium*, and wheat.

37. The transgenic plant or seed of claim 31, further comprising a second polynucleotide encoding a polypeptide of interest operably linked to the other end of the bidirectional promoter from the first polynucleotide.

\* \* \* \* \*